United States Patent
Takase et al.

(10) Patent No.: US 9,766,132 B2
(45) Date of Patent: Sep. 19, 2017

(54) MEASURING APPARATUS AND MEASURING METHOD

(71) Applicant: SCREEN Holdings Co., Ltd., Kyoto (JP)

(72) Inventors: Yasuhiro Takase, Kyoto (JP); Hidetoshi Nakanishi, Kyoto (JP); Motohiro Kono, Kyoto (JP); Kazuo Kinose, Kyoto (JP)

(73) Assignee: SCREEN Holdings Co., Ltd., Kyoto (JP)

( * ) Notice: Subject to any disclaimer, the term of this patent is extended or adjusted under 35 U.S.C. 154(b) by 0 days.

(21) Appl. No.: 15/017,730

(22) Filed: Feb. 8, 2016

(65) Prior Publication Data

US 2016/0245703 A1   Aug. 25, 2016

(30) Foreign Application Priority Data

Feb. 19, 2015 (JP) ................. 2015-030807

(51) Int. Cl.
*G01J 11/00* (2006.01)
*G01N 33/20* (2006.01)
(Continued)

(52) U.S. Cl.
CPC .......... *G01J 11/00* (2013.01); *G01N 21/3586* (2013.01); *G01N 21/8422* (2013.01);
(Continued)

(58) Field of Classification Search
CPC .............................. G01N 21/3581; G01J 11/00
See application file for complete search history.

(56) References Cited

U.S. PATENT DOCUMENTS

| 8,349,994 B2 | 1/2013 | Kadota et al. ............... 528/373 |
| 2004/0151957 A1* | 8/2004 | Brooks et al. ................. 429/20 |

(Continued)

FOREIGN PATENT DOCUMENTS

| EP | 2 811 285 | 10/2014 |
| JP | 2005-032668 | 2/2005 |

(Continued)

OTHER PUBLICATIONS

European search report issued Jul. 28, 2016 for the EPC counterpart of the above-mentioned application.
(Continued)

*Primary Examiner* — David Porta
*Assistant Examiner* — Hugh H Maupin
(74) *Attorney, Agent, or Firm* — Ostrolenk Faber LLP

(57) ABSTRACT

A measuring apparatus measure the amount of a metal catalyst supported on a sample that has a membrane of a metal catalyst layer containing the metal catalyst. The measuring apparatus includes a terahertz-wave emitting part that emits a terahertz wave in the range of 0.01 to 10 THz to the sample, a transmitted-terahertz-wave detection part that detects the electric field intensity of a transmitted terahertz wave that has passed through the sample, a storage that stores correlation information acquired in advance and indicating the correlation between the amount of the metal catalyst supported and the electric field intensity of the transmitted terahertz wave, and an amount-of-catalyst-supported acquisition module that acquires the amount of the metal catalyst supported on the sample, on the basis of the correlation information and the electric field intensity of the transmitted terahertz wave detected by the transmitted-terahertz-wave detection part.

6 Claims, 14 Drawing Sheets

(51) Int. Cl.
    *G01R 29/08*     (2006.01)
    *G01N 21/84*     (2006.01)
    *G01N 21/3586*   (2014.01)
(52) U.S. Cl.
    CPC ............ *G01N 33/20* (2013.01); *G01R 29/08* (2013.01); *G01N 2021/8427* (2013.01)

(56) References Cited

U.S. PATENT DOCUMENTS

2011/0097649 A1* 4/2011 Imamura et al. ............ 429/523
2012/0326037 A1  12/2012 Ohtake et al.
2013/0204577 A1  8/2013 Savard et al.
2013/0281290 A1  10/2013 Horiguchi et al. ............ 502/339
2014/0239182 A1* 8/2014 Ito et al. ....................... 250/351

FOREIGN PATENT DOCUMENTS

JP  2006-260909     9/2006
JP  2008-288093     11/2008
JP  2013-253981     12/2013
WO  WO 2012/090450 A1  7/2012

OTHER PUBLICATIONS

Withayachumnankul W et al. "T-Ray Sensing and Imaging", Proceedings of the IEEE, IEEE. New York, US, vol. 93, No. 8, Aug. 1, 2007, pp. 1528-1558, XP011193363.

* cited by examiner

F I G. 4
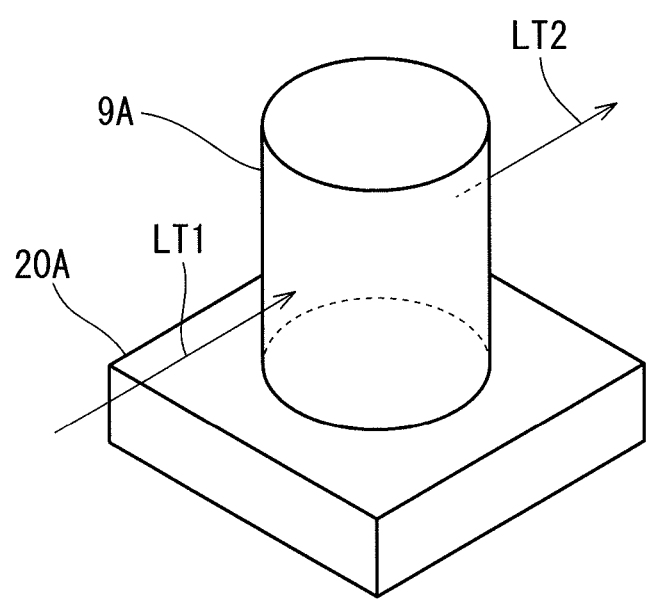

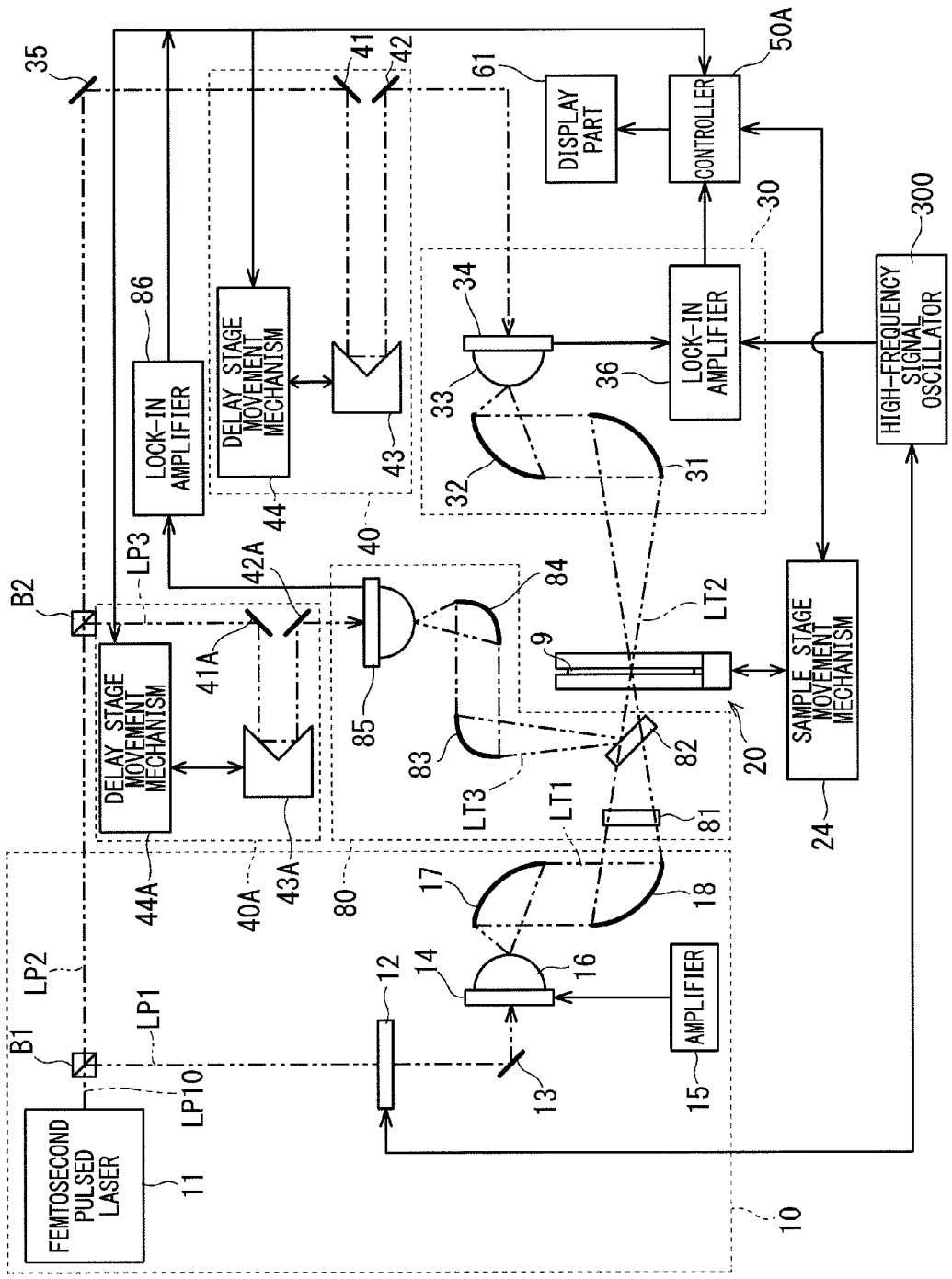
F I G. 12

F I G. 1 9
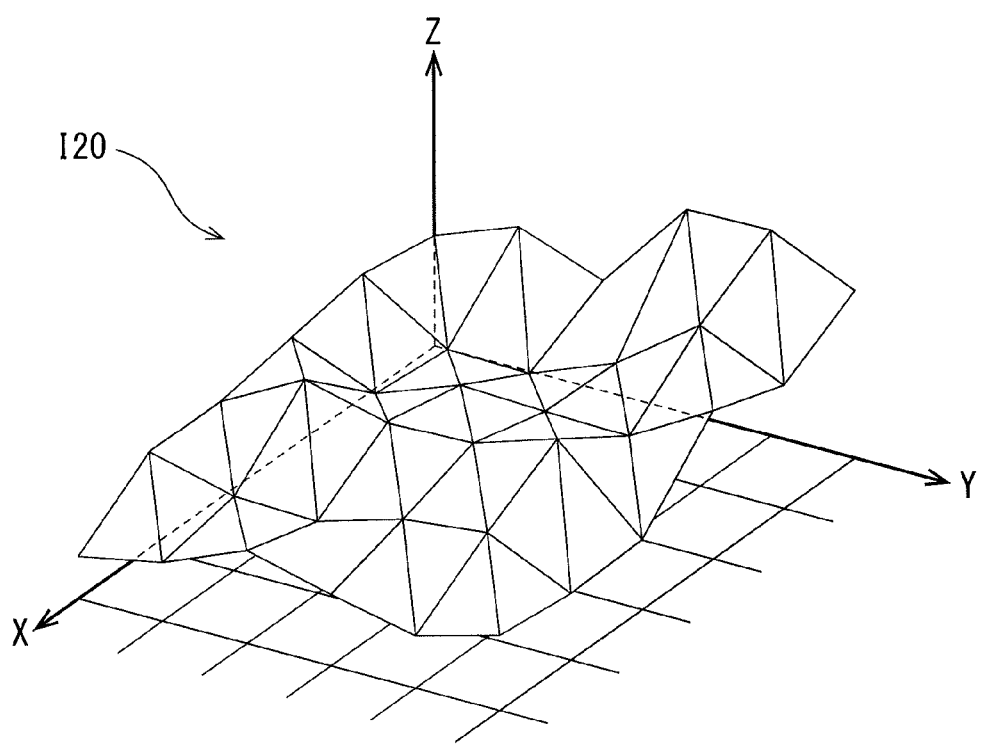

MEASURING APPARATUS AND MEASURING METHOD

BACKGROUND OF THE INVENTION

Field of the Invention

The present invention relates to a technique for measuring the amount of a catalyst supported on an object to be measured that has a metal catalyst layer.

Description of the Background Art

Solid polymer electrolyte fuel cells (hereinafter, also abbreviated as "PEFCs") are fuel cells including a polyelectrolyte. For example, an ion exchange resin is used as an example of a solid polyelectrolyte. In a PEFC, positive and negative electrodes are located with the solid polyelectrolyte in between them, and hydrogen is supplied as a fuel to the negative electrode and oxygen or air is supplied to the positive electrode to cause electrochemical reactions and produce electricity.

For example, the use of hydrogen as a fuel causes a reaction expressed by the following formula at the negative electrode:

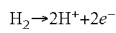

$H_2 \rightarrow 2H^+ + 2e^-$

The use of oxygen as an oxidant causes a reaction expressed by the following formula and produces water at the positive electrode.

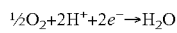

$\frac{1}{2}O_2 + 2H^+ + 2e^- \rightarrow H_2O$

To maximize those reactions at the positive and negative electrode of the fuel cell, a catalyst layer that is mixed with the positive and negative electrodes is important.

Japanese Patent Application Laid-Open No. 2005-32668 relates to an improvement in the performance of a catalyst layer and describes that the amount of platinum to be used is controlled depending on the concentration and membrane thickness in the preparation of a carbon paste that supports a platinum catalyst. the distribution of membrane thicknesses or discrepancy caused by uneven distribution of platinum nanoparticles in the catalyst layer as a result of a coating process are examined using a fuel cell, which is an end product.

Japanese Patent Application Laid-Open No. 2008-288093 relates to an improvement in the performance of an electrolyte membrane. A catalyst layer is produced using a commonly-known method, and the distribution of membrane thicknesses or discrepancy caused by uneven distribution of platinum nanoparticles in the catalyst layer obtained as a result of a coating process are examined using a fuel cell, which is an end product.

In Japanese Patent Application Laid-Open No. 2005-32668, platinum and a platinum alloy are used as catalysts of a fuel cell, and the catalysts are supported on, for example, carbon black.

In International Publication WO 2012/090450, platinum serving as a catalyst is supported on a platinum colloid, and colloidal particles are supported on, for example, carbon black.

In Japanese Patent Application Laid-Open No. 2006-260909, a palladium alloy (palladium-cobalt alloy) using a non-platinum metal as a catalyst is supported on, for example, carbon black.

Since platinum and platinum alloys suggested by Japanese Patent Application Laid-Open Nos. 2005-32668 and 2008-288093 are rare and expensive and greatly affect the performance of fuel cells, the catalyst needs to be supported in proper amounts. Thus, examining discrepancies after the manufacture of cells as end products may be a big economic loss.

Non-platinum metal materials suggested by International Publication No. WO 2012/090450 are less expensive than platinum, but still needs to be supported in proper amounts because they greatly affect the performance of fuel cells. Thus, again, examining discrepancies after the manufacture of fuel cells as end products may be a big economic loss.

SUMMARY OF THE INVENTION

A first aspect is directed to a measuring apparatus for measuring an amount of a metal catalyst supported on an object to be measured, the object having a membrane of a metal catalyst layer containing the metal catalyst. The measuring apparatus includes a terahertz-wave emitting part that emits a terahertz wave in a range of 0.01 to 10 THz to an object to be measured, a transmitted-terahertz-wave detection part that detects an electric field intensity of a transmitted terahertz wave that is the terahertz wave that has passed through the object to be measured, a storage that stores correlation information that is acquired in advance and indicates a correlation between the amount of the metal catalyst supported on the object to be measured and the electric field intensity of the transmitted terahertz wave, and an amount-of-catalyst-supported acquisition part that acquires the amount of the metal catalyst supported on the object to be measured, on the basis of the correlation information and the electric field intensity of the transmitted terahertz wave detected by the transmitted-terahertz-wave detection part.

The measuring apparatus of this aspect is capable of measuring the amount of a catalyst supported at the time of forming the metal catalyst layer. Thus, excess and deficiency of the amount of a catalyst supported can be examined before the manufacture of fuel cells as end products. This reduces the occurrence of economic losses.

In a second aspect, in the measuring apparatus of the first aspect, the terahertz-wave emitting part includes a terahertz wave generator that generates the terahertz wave in a pulsed form upon receipt of first pulsed light, and the transmitted-terahertz-wave detection part includes a transmitted terahertz wave detector that detects the electric field intensity of the transmitted terahertz wave upon receipt of second pulsed light. The measuring apparatus further includes a delay part that delays a time when the second pulsed light is incident on the transmitted terahertz wave detector with respect to a time when the first pulsed light is incident on the terahertz wave generator.

According to the second aspect, the electric field intensity of the transmitted terahertz wave can be acquired for each different phase by delaying the second pulsed light with respect to the first pulsed light.

In a third aspect, the measuring apparatus of the second aspect further includes a peak-intensity identification part that identifies a peak intensity of the electric field intensity of the transmitted terahertz wave on the basis of electric field intensities of the transmitted terahertz wave that are acquired for different phases by controlling the delay part. The amount-of-catalyst-supported acquisition part acquires the amount of the metal catalysts supported on the object to be measured, on the basis of the peak intensity and the correlation information.

According to the third aspect, the amount of a catalyst supported on the object to be measured can be measured on the basis of the peak intensity of the transmitted terahertz wave that has a strong correlation with the amount of a catalyst supported.

In a fourth aspect, the measuring apparatus of one of the first to third aspects further includes an amount-of-catalyst-supported distribution image generation part that generates an image of a distribution of the amount of the metal catalyst supported acquired by the amount-of-catalyst-supported acquisition part, on the basis of the electric field intensity of the transmitted terahertz wave that is acquired by scanning a surface of the object to be measured with the terahertz wave.

According to the fourth aspect, the imaging of the distribution of the amounts of a catalyst supported enables visual recognition of the distribution of the amounts of a catalyst supported.

In a fifth aspect, the measuring apparatus of one of the first to fourth aspects further includes a reflected-terahertz-wave detection part that detects an electric field intensity of a reflected terahertz wave that is the terahertz wave that is reflected from the object to be measured, and a reflection-position information acquisition part that acquires information regarding a reflection position in a direction of membrane thickness of the object to be measured from which the terahertz wave is reflected, on the basis of the electric field intensity of the reflected terahertz wave.

According to the fifth aspect, the position of the center of gravity of the metal catalyst in the direction of membrane thickness can be measured by acquiring the reflection position of the terahertz wave.

In a sixth aspect, the measuring apparatus of the fifth aspect further includes a reflection-position distribution image generation part that generates an image of a distribution of the reflection position acquired by the reflection-position information acquisition part, on the basis of the reflected terahertz wave detected by scanning a surface of the object to be measured with the terahertz wave.

According to the sixth aspect, the imaging of the distribution of the reflection positions enables visual recognition of the distribution of the positions of the center of gravity of the metal catalyst.

A seventh aspect is directed to a measuring method of measuring an amount of a metal catalyst supported on an object to be measured, the object having a metal catalyst layer containing the metal catalyst. The measuring method includes (a) a terahertz-wave emitting step of emitting a terahertz wave in a range of 0.01 to 10 THz to an object to be measured, (b) a transmitted-terahertz-wave detection step of detecting an electric field intensity of a transmitted terahertz wave that is the terahertz wave that has passed through the object to be measured, (c) a readout step of reading out correlation information that is stored in advance in a storage and indicates a correlation between the amount of the metal catalyst supported on the object to be measured and the electric field intensity of the transmitted terahertz wave, and (d) an amount-of-catalyst-supported acquisition step of acquiring the amount of the metal catalyst supported on the object to be measured, on the basis of the correlation information and the electric field intensity of the transmitted terahertz wave acquired in the transmitted-terahertz-wave detection step.

Thus, it is an object of the present invention is to provide a technique for measuring the amount of a metal catalyst supported on a fuel cell while reducing the occurrence of economic losses.

These and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a schematic perspective view of a sample stage according to a variation of the first preferred embodiment;

FIG. 12 is a schematic configuration diagram of a measuring apparatus according to a third preferred embodiment;

FIG. 19 illustrates an exemplary reflection-position distribution image according to the third preferred embodiment.

DESCRIPTION OF THE PREFERRED EMBODIMENTS

Figure 1:
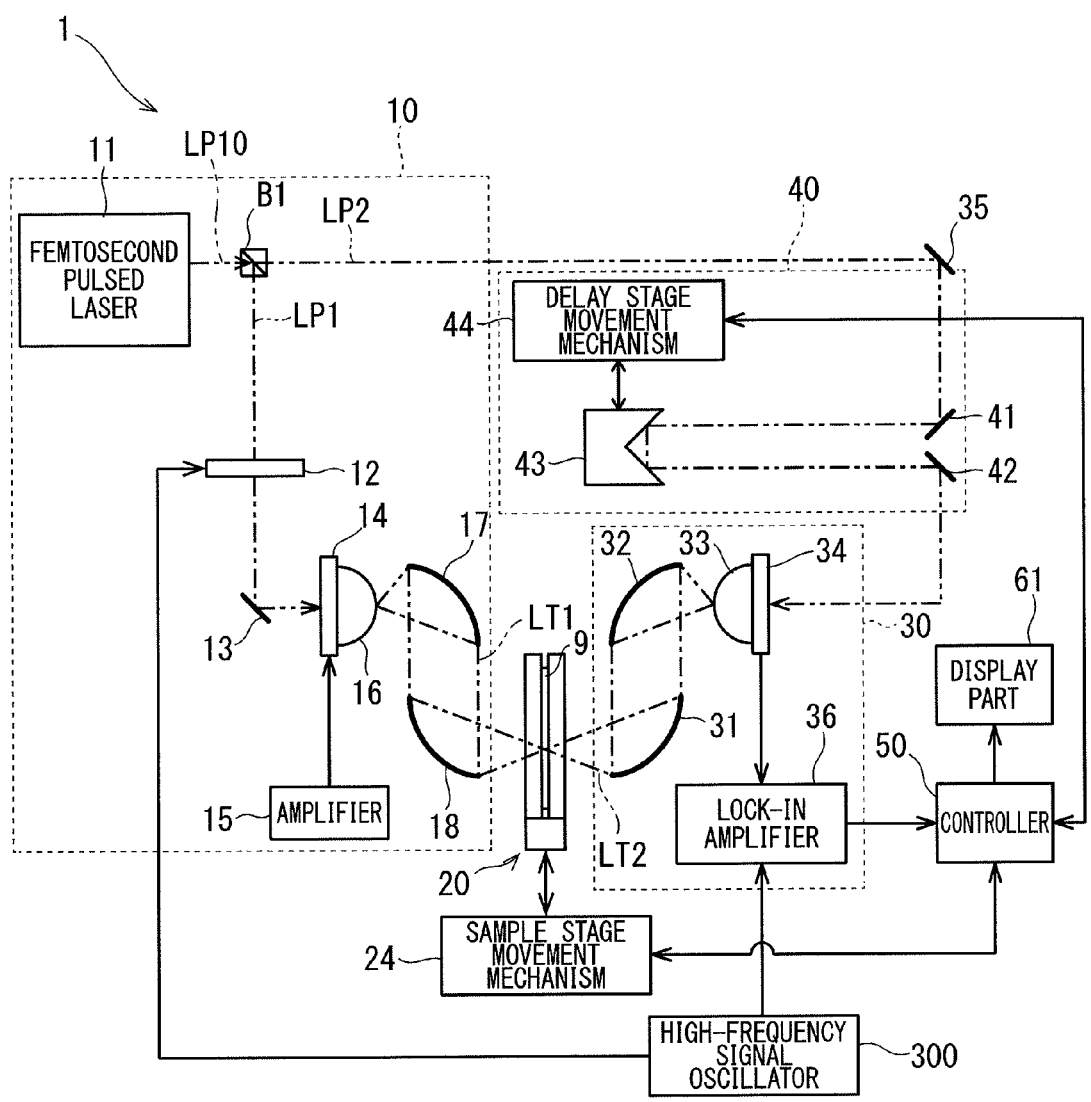
FIG. 1 is a schematic configuration diagram of a measuring apparatus according to a first preferred embodiment.

Preferred embodiments according to the present invention will now be described with reference to the accompanying drawings. Components described in the preferred embodiments are merely illustrative, and there is no intention to limit the scope of the present invention thereto. In the drawings, the dimensions of components and the number of components are shown in exaggeration or in simplified form, as appropriate, for the sake of easier understanding.

1. First Preferred Embodiment

FIG. 1 is a schematic configuration diagram of a measuring apparatus 1 according to a first preferred embodiment. The measuring apparatus 1 includes a terahertz-wave emitting part 10, a sample stage 20, a transmitted-terahertz-wave detection part 30, a delay part 40, and a controller 50. The measuring apparatus 1 is configured as an apparatus that measures the amount of a metal catalyst supported on a sample 9 (object to be measured) having a membrane containing the metal catalyst.

Terahertz-Wave Emitting Part

The terahertz-wave emitting part 10 is configured to emit a terahertz wave LT1 to a sample 9 that is supported on the sample stage 20.

The terahertz-wave emitting part 10 includes a femtosecond pulsed laser 11.

The femtosecond pulsed laser 11 emits, for example, pulsed laser light (pulsed light LP10) with wavelengths in the range of 360 nanometers (nm) to 1.5 micrometers (μm), including a visible light range. As one example, the femtosecond pulsed laser 11 is configured to emit linearly polarized pulsed light LP10 with a center wavelength of approximately 800 nm, a frequency of several to several hundred kilohertz, and a pulse width of approximately 10 to 150 femtoseconds. The femtosecond pulsed laser 11 may also be configured to emit pulsed light LP10 with wavelengths in other wavelength regions (e.g., visible light wavelengths such as blue wavelengths (450 to 495 nm) and green wavelengths (495 to 570 nm)).

The pulsed light LP10 emitted from the femtosecond pulsed laser 11 is divided into two by a beam splitter B1, one being pump light LP1 (first pulsed light) and the other being probe light LP2 (second pulsed light). The pump light LP1 is incident on a photoconductive switch 14 on the emitter side through, for example, a chopper 12 controlled by a high-frequency signal oscillator 300 and a plane mirror 13. The photoconductive switch 14 receives a bias voltage applied by an amplifier 15, and produces a pulsed terahertz wave LT1 in response to the incidence of the pulsed pump light LP1. The photoconductive switch 14 is one example of a terahertz wave generator for generating terahertz waves.

The frequency of the terahertz wave produced by the photoconductive switch 14 is generally determined by the shape of the photoconductive switch 14. For example, the photoconductive switch 14 of a dipole shape produces terahertz waves in the range of 0.1 to 4 THz, and the photoconductive switch 14 of a bowtie shape produces terahertz waves in the range of 0.03 to 2 THz. In the measuring apparatus 1, the terahertz wave LT1 may include terahertz waves in the range of 0.01 to 10 THz.

The terahertz wave LT1 produced by the photoconductive switch 14 is diffused through a hyper-hemispherical silicon lens 16. The terahertz wave LT1 is then collimated by a parabolic mirror 17 and converges to a parabolic mirror 18. Then, the sample 9 placed at the focal position of the parabolic mirror 18 is irradiated with the terahertz wave LT1.

The terahertz-wave emitting part 10 may be configured in any way as long as it can irradiate the sample 9 with the terahertz wave LT1. For example, the pump light LP1 emitted from the femtosecond pulsed laser 11 may be incident on the photoconductive switch 14 through an optical-fiber cable. A configuration is also possible in which the parabolic mirror 18 is omitted, the distance between the photoconductive switch 14 and the parabolic mirror 17 is reduced, and the sample 9 is placed at a focal position to which the terahertz wave LT1 reflected by the parabolic mirror 17 converges. Also, one or both of the parabolic mirrors 17 and 18 may be replaced by a terahertz lens.

Sample Stage

Figure 2:
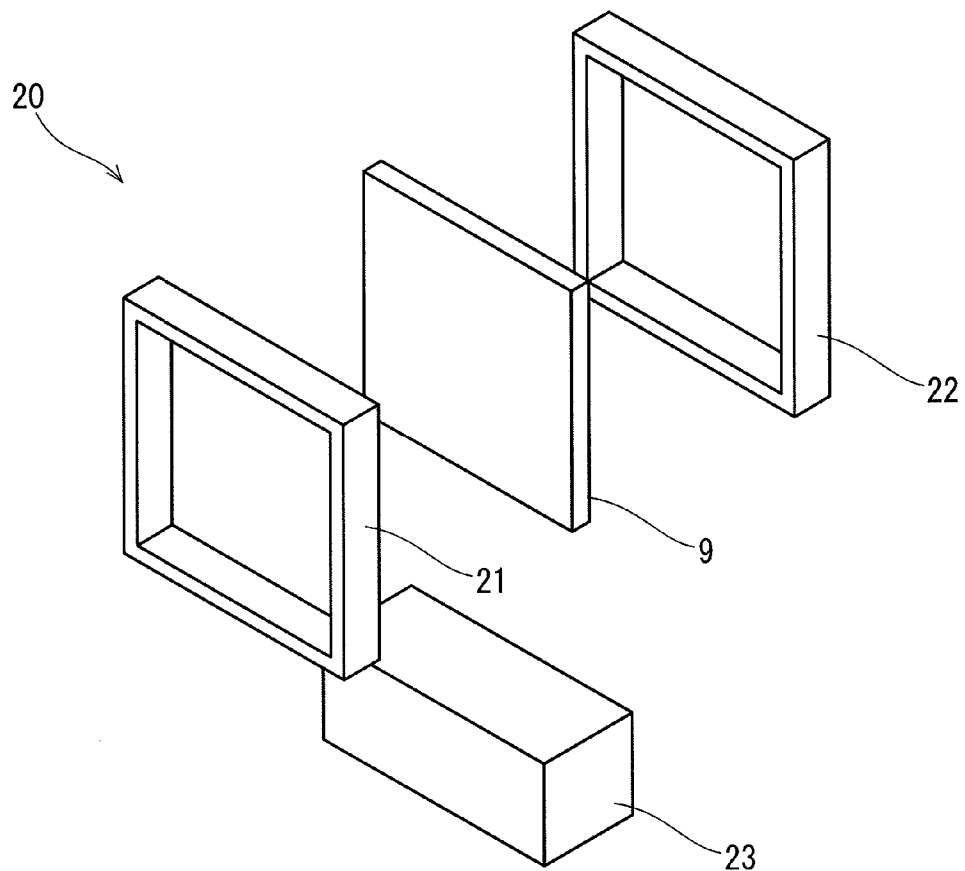
FIG. 2 is an exploded schematic perspective view of a sample stage according to the first preferred embodiment.
Figure 3:
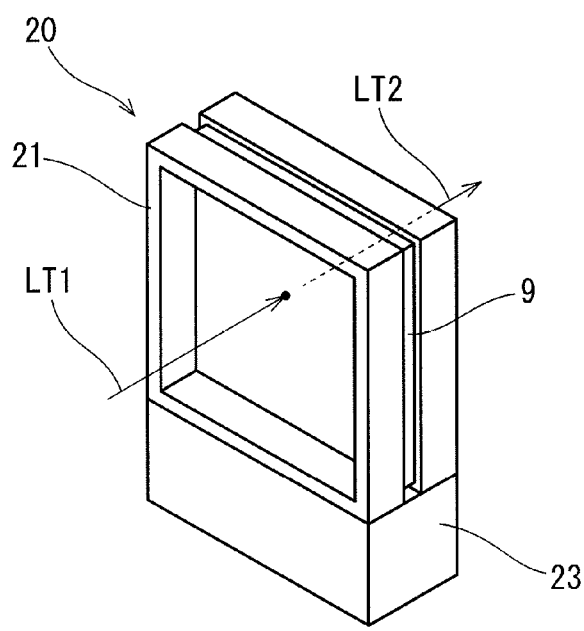
FIG. 3 is a schematic perspective view illustrating the sample stage of the first preferred embodiment that holds a sample.

FIG. 2 is an exploded schematic perspective view of the sample stage 20 according to the first preferred embodiment. FIG. 3 is a schematic perspective view of the sample stage 20 of the first preferred embodiment that holds the sample 9.

The sample stage 20 grasps the sample 9 perpendicular to the travel direction of the terahertz wave LT1 and at the focal positions of the parabolic mirror 18 and a parabolic mirror 31, which will be described later. To be more specific, the sample stage 20 includes support element for supporting the sample 9 in accordance with the shape of the sample 9. As one example, when the sample 9 is a catalyst coated membrane (CCM) that is an electrode membrane for fuel cells including a catalyst layer and an electrolyte membrane, the sample stage 20 may be provided with sample retaining frames 21 and 22 as illustrated in FIGS. 2 and 3. With the periphery of the sample 9 grasped by the sample retaining frames 21 and 22, the sample retaining frames 21 and 22 are, for example, screwed and further fastened in an upright position to a pedestal 23 of the sample stage 20.

Note that the size of the inner hollow cavities of the sample retaining frames 21 and 22 is desirably greater than the spot diameter of the terahertz wave LT1, but may also be smaller than the spot diameter if the terahertz wave is detectable with the transmitted-terahertz-wave detection part 30, which will be described later.

FIG. 4 is a schematic perspective view of a sample stage 20A according to a variation of the first preferred embodiment. When a sample is difficult to grasp with the sample retaining frames 21 and 22 due to its uneven thickness as in the case of the sample 9A in FIG. 4, it is also conceivable to dispose the sample 9A on the sample stage 20A having a horizontal surface.

As illustrated in FIG. 1, the sample stage 20 is connected to a sample stage movement mechanism 24. The sample stage movement mechanism 24 moves the sample stage 20 to move the sample 9 in one axial direction or in two axial directions orthogonal to each other in a plane perpendicular to the travel direction of the terahertz wave LT1. A conceivable example of the configuration of the sample stage movement mechanism 24 is such that the stage is moved in an axial direction by, for example, an electric sliding mechanism that causes a linear motor or a screw shaft engaged with a nut member on the slider side to be rotationally driven by servo motor drive, and the amount of travel of the sample stage 20 is measured with, for example, a linear gauge.

The sample stage movement mechanism 24 is controlled by a sample stage control module 501 (FIG. 5) of the controller 50. The measuring apparatus 1 is configured to be able to measure the amount of a catalyst supported, at a plurality of points on the sample 9 by causing the sample stage 20 to move.

Note that the optical path of the terahertz wave LT1 itself may be changed to allow different points on the sample 9 to be irradiated with the terahertz wave. More specifically, it is conceivable to use a galvanometer mirror that oscillates reciprocally to change the optical path of the terahertz wave LT1 in parallel with the surface of the sample 9. Instead of the galvanometer mirror, other means such as a polygon mirror, a piezo mirror, and an acoustooptic device may be employed.

Transmitted-Terahertz-Wave Detection Part

The transmitted-terahertz-wave detection part 30 detects the electric field intensity of a transmitted terahertz wave LT2 that is the terahertz wave LT1 that has passed through the sample 9.

The transmitted terahertz wave LT2 that has passed through the sample 9 is collimated by a parabolic mirror 31 located at a position that is away from the sample 9 by the focal length of the parabolic mirror 31. The collimated transmitted terahertz wave LT2 is then caused to converge to the parabolic mirror 32. The transmitted terahertz wave is then incident on a photoconductive switch 34 through a hyper-hemispherical silicon lens 33. The photoconductive switch 34 is located at a position corresponding to the focal length of the parabolic mirror 32.

Out of the beam fluxes emitted from the femtosecond pulsed laser 11 and divided into two by the beam splitter B1, the other probe light LP2 (second pulsed light) is incident on the photoconductive switch 34 through a plane mirror 35 and the delay part 40. When the probe light LP2 is received, current that corresponds to the electric field intensity of the transmitted terahertz wave LT2 incident on the photoconductive switch 34 flows through the photoconductive switch 34. A change in voltage at this time is amplified by a lock-in amplifier 36 and incorporated in the controller 50 at a frequency in accordance with the high-frequency signal oscillator 300 via a predetermined interface. The photoconductive switch 34 is one example of a transmitted-terahertz-wave detector for detecting the electric field intensity of the transmitted terahertz wave LT2.

Note that one or both of the parabolic mirrors 31 and 32 may be replaced by a terahertz lens. A configuration is also possible in which the parabolic mirror 32 is omitted, the distance between the sample 9 and the parabolic mirror 31 is reduced to less than the focal length of the parabolic mirror 31, and the photoconductive switch 34 is located at the focal position of the parabolic mirror 31 to allow the transmitted terahertz wave LT2 to be incident on the photoconductive switch 34.

Delay Part

The delay part 40 delays the time when the probe light LP2 is incident on the photoconductive switch 34 serving as a transmitted-terahertz-wave detector with respect to the time when the pump light LP1 is incident on the photoconductive switch 14 serving as a terahertz wave oscillator.

To be more specific, the delay part 40 includes plane mirrors 41 and 42, a delay stage 43, and a delay stage movement mechanism 44. The probe light LP2 is reflected by the plane mirror 35 and then reflected by the plane mirror 41 toward the delay stage 43. The delay stage 43 includes a return mirror that returns the incident probe light LP2 in the opposite direction to the direction of incidence of the probe light LP2. The probe light LP2 returned from the delay stage 43 is reflected by the plane mirror 42 and is then incident on the photoconductive switch 34.

The delay stage 43 is moved in parallel with the direction of incidence of the probe light LP2 by the delay stage movement mechanism 44. An exemplary configuration of the delay stage movement mechanism 44 is such that the delay stage 43 is moved in an axial direction by, for example, an electric sliding mechanism that causes a linear motor or a screw shaft engaged with a nut member on the slider side to be rotationally driven by servo motor drive, and the amount of travel of the delay stage 43 is measured with, for example, a linear gauge.

By linearly moving the delay stage 43 in parallel with the probe light LP2, it is possible to change the optical path length of the probe light LP2 from the femtosecond pulsed laser 11 to the photoconductive switch 34. Thus, the timing of when the probe light LP2 is incident on the photoconductive switch 34 can be changed. In other words, it is possible to change the timing (phase) of when the photoconductive switch 34 detects the electric field intensity of the transmitted terahertz wave LT2.

Note that the delay part 40 may be provided on the optical path of the pump light LP1 (first pulsed light). That is, the timing of when the pump light LP1 reaches the photoconductive switch 34 can be delayed by changing the optical path length of the pump light LP1. With this configuration, it is possible to change the timing of when the pulsed terahertz wave LT1 is produced and to change the timing (phase) of when the photoconductive switch 34 detects the electric field intensity of the transmitted terahertz wave LT2.

Controller

Figure 5:
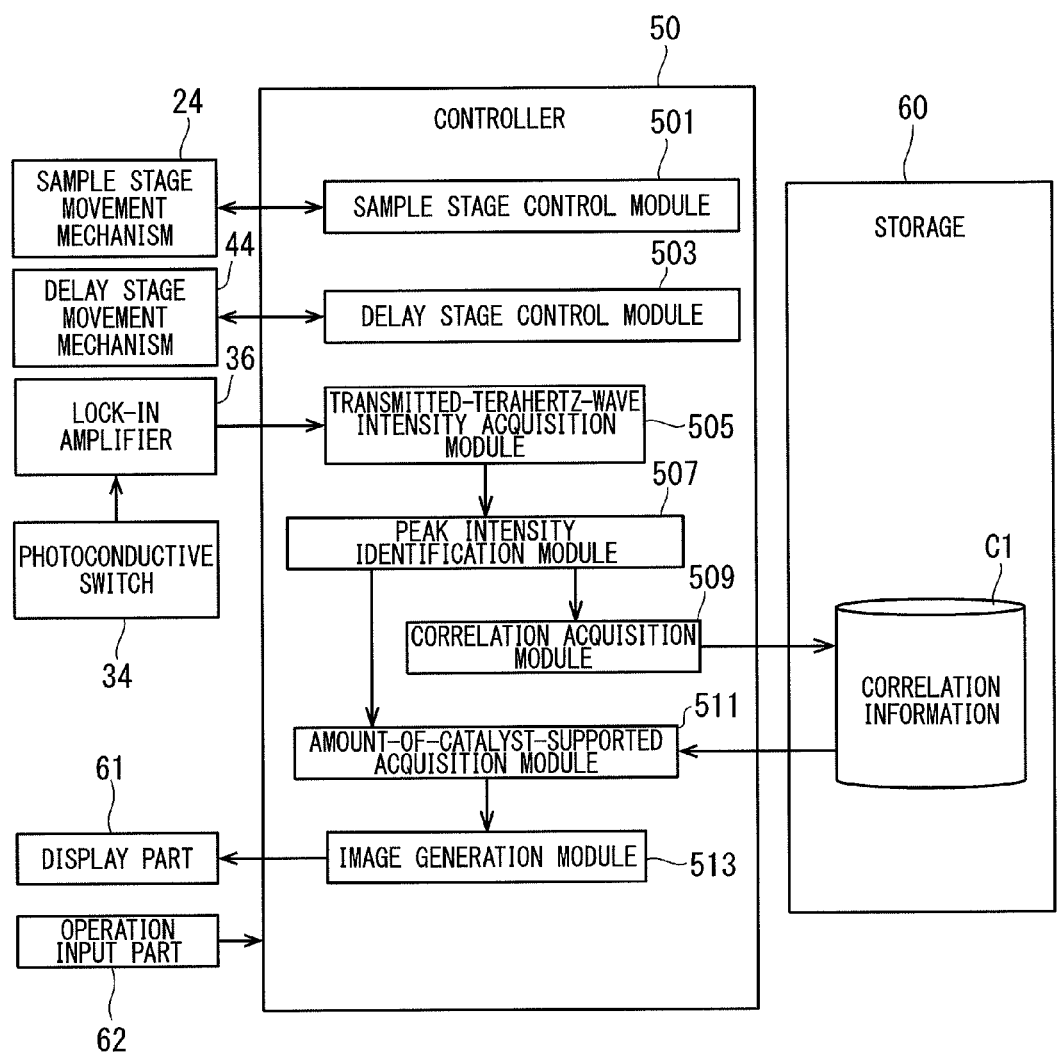
FIG. 5 is a block diagram illustrating a configuration of a controller according to the first preferred embodiment.

FIG. 5 is a block diagram illustrating a configuration of the controller 50 according to the first preferred embodiment. Although not shown, the controller 50 is configured as a general computer that includes, for example, a CPU, a ROM, and a RAM.

Modules illustrated in FIG. 5, including a sample stage control module 501, a delay stage control module 503, a transmitted-terahertz-wave intensity acquisition module 505, a peak intensity identification module 507, a correlation acquisition module 509, an amount-of-catalyst-supported acquisition module 511, and an image generation module 513, are functions that are each implemented by the CPU of the controller 50 operating in accordance with a program not shown. Note that some or all of these functions may be implemented by hardware such as dedicated circuits.

The sample stage control module 501 is configured to control the sample stage movement mechanism 24. The delay stage control module 503 is configured to control the delay stage movement mechanism 44.

The transmitted-terahertz-wave intensity acquisition module 505 is configured to read the value of a voltage generated by the photoconductive switch 34 via the lock-in amplifier 36 to acquire the electric field intensity of the transmitted terahertz wave LT2. As a result of the delay stage control module 503 moving the delay stage 43 of the delay part 40, the transmitted-terahertz-wave intensity acquisition module 505 acquires the electric field intensity of the transmitted terahertz wave LT2 with different timings (phases).

The peak intensity identification module 507 is configured to identify the peak intensity of the electric field intensity of the transmitted terahertz wave on the basis of the electric field intensities acquired for different phases of the transmitted terahertz wave LT2 by the transmitted-terahertz-wave intensity acquisition module 505.

The correlation acquisition module 509 is configured to acquire correlation information C1 that indicates the correlation between the amount of a metal catalyst (hereinafter, referred to as the "amount of a catalyst supported") included in a membrane of the metal catalyst layer formed on the sample 9 and the transmitted terahertz wave LT2 that has passed through the sample 9. The correlation information C1 is stored in a storage 60, which includes nonvolatile storages such as a hard disk, an optical disk, and a magneto-optic disk and other storages such as a RAM that temporarily stores information, and is readable by the amount-of-catalyst-supported acquisition module 511.

As will be described later, in the measuring apparatus 1, the electric field intensity of the transmitted terahertz wave LT2 is measured in advance for each sample (hereinafter, also referred to as a "reference sample") that includes a metal catalyst layer with a known amount of a catalyst supported, and the peak intensity identification module 507 identifies the peak intensity of the transmitted terahertz wave LT2 that corresponds to each amount of a catalyst supported. The correlation acquisition module 509 acquires the correlation information C1 that identifies the correlation between the amount of a catalyst supported on each reference sample and the peak intensity acquired for the reference sample.

The correlation information C1 may be data in the form of a correspondence table in which the peak intensity of the transmitted terahertz wave LT2 is recorded for each of several amounts of a catalyst supported, or may be data in the form of a relational expression between the amount of a catalyst supported and the electric field intensity of the transmitted terahertz wave LT2.

The amount-of-catalyst-supported acquisition module 511 is configured to acquire the amount of a metal catalyst supported on the sample 9 on the basis of the correlation information C1 stored in the storage unit 60 and the electric field intensity of the transmitted terahertz wave LT2 that has passed through the sample 9.

The image generation module 513 is configured to display a measured result of the amount of a catalyst supported, acquired by the amount-of-catalyst-supported acquisition module 511, on a display part 61. For example, the distribution of the electric field intensities of the transmitted terahertz wave LT2 is acquired by scanning the surface of the sample 9 with the terahertz wave LT1. On the basis of this distribution of the electric field intensities, the amount-of-catalyst-supported acquisition module 511 acquires the distribution of the amounts of a metal catalyst supported. The image generation module 513 generates an image of the distribution of the amounts of a catalyst supported by expressing the magnitude of the amount of a catalyst supported in different colors or patterns. The image generation module 513 is one example of an amount-of-catalyst-supported distribution image generation part.

The controller 50 is connected to the display part 61 and an operation input part 62. The display part 61 is configured by, for example, a liquid crystal display and displays various measured results (e.g., images generated by the image generation module 513 and time waveforms of the transmitted terahertz wave LT2, and frequency spectrums). The operation input part 62 is an input device configured by, for example, a keyboard and a mouse and receives input of various operations (operations for inputting commands and various types of data) from an operator. More specifically, the operation input part 62 receives input of operations including an operation of selecting an operation mode of the measuring apparatus 1 (including a correlation-information acquisition mode and an amount-of-catalyst-supported measuring mode) and an operation of designating a point (measurement range) to be measured on the sample 9. Note that the operation input part 62 may be configured by, for example, various types of switches and a touch panel.

Operations of Measuring Apparatus

Figure 6:
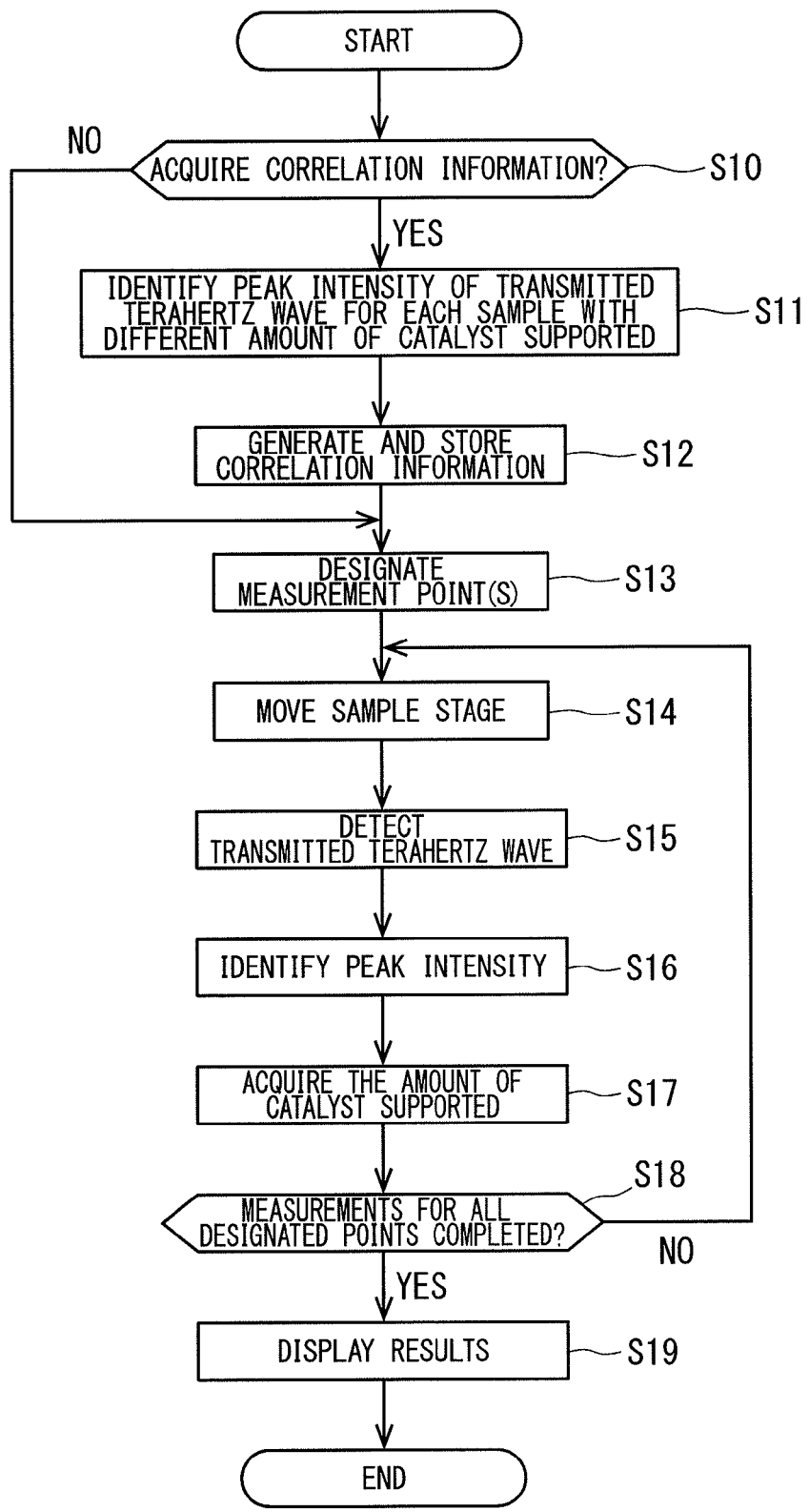
FIG. 6 is a flowchart illustrating a procedure of operations performed by the measuring apparatus according to the first preferred embodiment.

FIG. 6 is a flowchart illustrating a procedure of operations performed by the measuring apparatus 1 according to the first preferred embodiment. Note that the operations of the measuring apparatus 1 described below are performed under the control of the controller 50, unless otherwise specified.

First, the controller 50 determines on the basis of an operator's instruction whether or not to acquire the correlation information C1 (step S10). If YES in step S10, the procedure proceeds to step S11 and the measuring apparatus 1 operates in the correlation-information acquisition mode for acquiring the correlation information C1. On the other hand, if NO in step S10, the procedure proceeds to step S13 and the measuring apparatus 1 operates in the amount-of-catalyst-supported measuring mode for measuring the amount of a catalyst supported.

Correlation-Information Acquisition Mode

In the correlation-information acquisition mode, each of a plurality of reference samples having different amounts of a catalyst supported is irradiated with the terahertz wave LT1 to measure the electric field intensity of the transmitted terahertz wave LT2. Note that the reference samples and the sample 9 that is to be measured by the measuring apparatus 1 have a common structure, except in that the amounts of a catalyst supported on the reference samples are known. Then, the peak intensity of the transmitted terahertz wave LT2 for each reference sample is identified by the peak intensity identification module 507 (step S11). Then, on the basis of the peak intensity acquired in step S11 and the amount of a catalyst supported used in measurement, the correlation information C1 that defines the correlation between the peak intensity and the amount of a catalyst supported is generated and stored in the storage unit 60 by the correlation acquisition module 509 (step S12).

Figure 7:
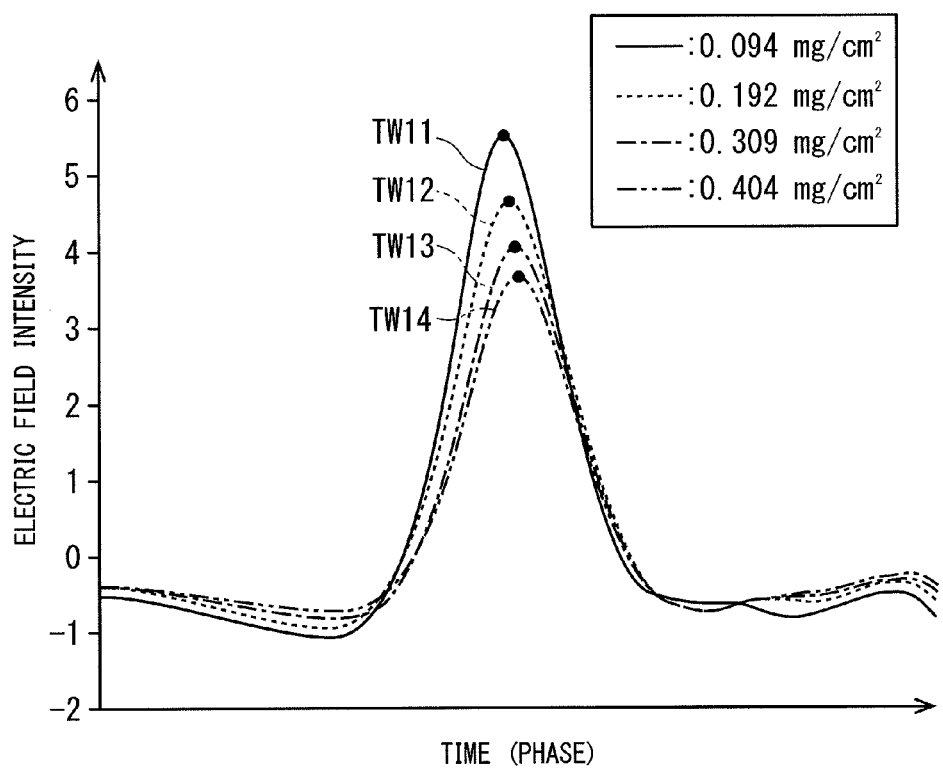
FIG. 7 illustrates time waveforms for transmitted terahertz waves that have passed through reference samples with different amounts of a catalyst supported.

FIG. 7 illustrates time waveforms TW11 to TW14 of the transmitted terahertz wave LT2 that has passed through reference samples with different amounts of a catalyst supported. In FIG. 7, the horizontal axis indicates time, and the vertical axis indicates electric field intensity. The time waveforms TW11 to TW14 illustrated in FIG. 7 correspond to the transmitted terahertz wave LT2 that has respectively passed through the reference samples with the amounts of platinum supported of 0.094, 0.192, 0.309, and 0.404 mg/cm$^2$.

As illustrated in FIG. 7, the peak intensity, which is the maximum electric field intensity, gradually decreases as the amount of platinum supported increases. More specifically, the peak intensities (relative values) of the time waveforms TW11 to TW14 are respectively 5.544, 4.655, 4.047, and 3.676 and the correlation coefficient is −0.98. In this way, the amount of platinum supported and the peak intensity of the transmitted terahertz wave LT2 have a very strong negative correlation.

As described above, the relational expression between the amount of a catalyst supported and the peak intensity of the transmitted terahertz wave may be used as the correlation information C1. As one example, a regression equation (y=−0.1639x+0.9849) can be derived through regression analysis based on the results in FIG. 7, where the amount of platinum supported is a dependent variable and the peak intensity is an explanatory variable. This regression equation may be stored as the correlation information C1 in the storage unit 60. As another alternative, the peak intensities obtained through measurement and the amounts of a catalyst supported may be plotted on two-dimensional coordinates, and interpolation curves obtained by connecting plotted points with curves may be used as the correlation information C1.

Figure 8:
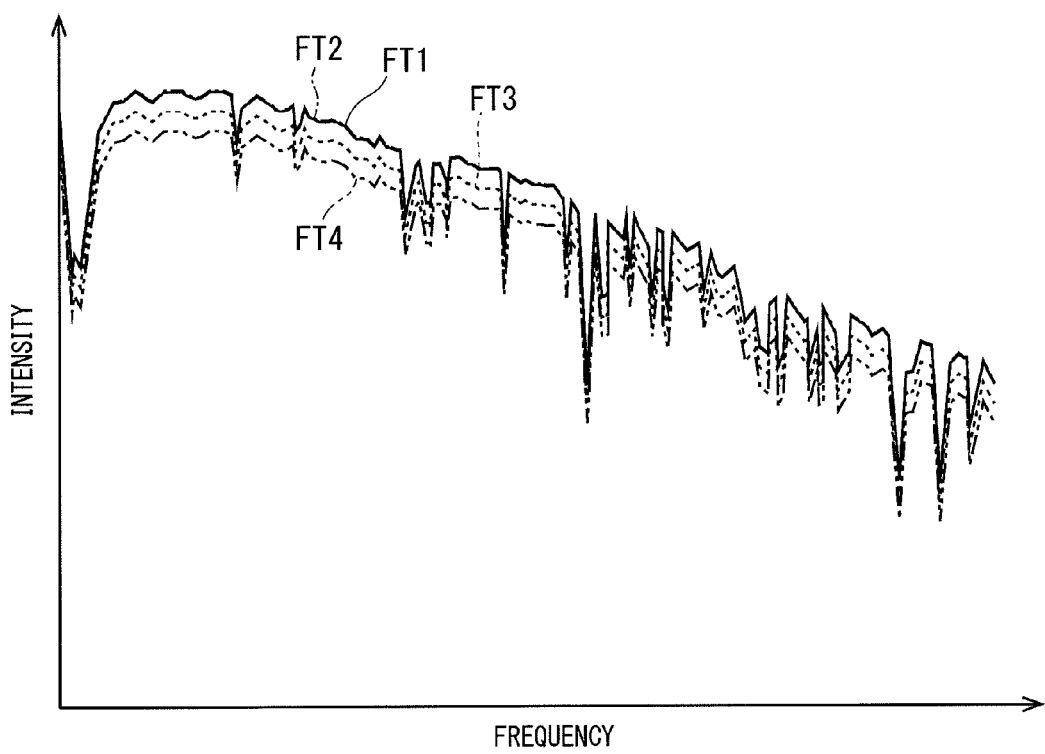
FIG. 8 illustrates frequency distributions for the transmitted terahertz waves that have passed through the reference samples with different amounts of a catalyst supported.

FIG. 8 illustrates frequency distributions FT1 to FT4 of the transmitted terahertz wave LT2 that has passed through reference samples having different amounts of a catalyst supported. In FIG. 8, the horizontal axis indicates frequency, and the vertical axis indicates intensity. The frequency distributions FT1 and FT2 illustrated in FIG. 8 indicate frequency distributions of the transmitted terahertz wave LT2 that has passed through reference samples with membranes that do not contain a metal catalyst (platinum). The thicknesses of the membranes are respectively set to dimensions that correspond respectively to expected dimensions when the amounts of a catalyst supported are 0.15 and 0.35 mg/cm$^2$. The frequency distributions FT3 and FT4 indicate frequency distributions for the transmitted terahertz wave LT2 that has passed through reference samples with membranes respectively having the amounts of a metal catalyst (platinum) supported of 0.192 and 0.404 mg/cm$^2$.

As indicated by the frequency distributions FT1 and FT2, the reference samples that do not contain platinum have little difference in the frequency components of the transmitted terahertz wave, even if their membranes have different thicknesses. The frequency distributions FT3 and FT4 indicate that the intensity (dB) of each frequency decreases as the amount of platinum as a metal catalyst supported increases. That is, it can be thought that the peak intensity of the transmitted terahertz wave LT2 little depends on the membrane thickness and depends on the amount of a metal catalyst (platinum) supported.

Figure 9:
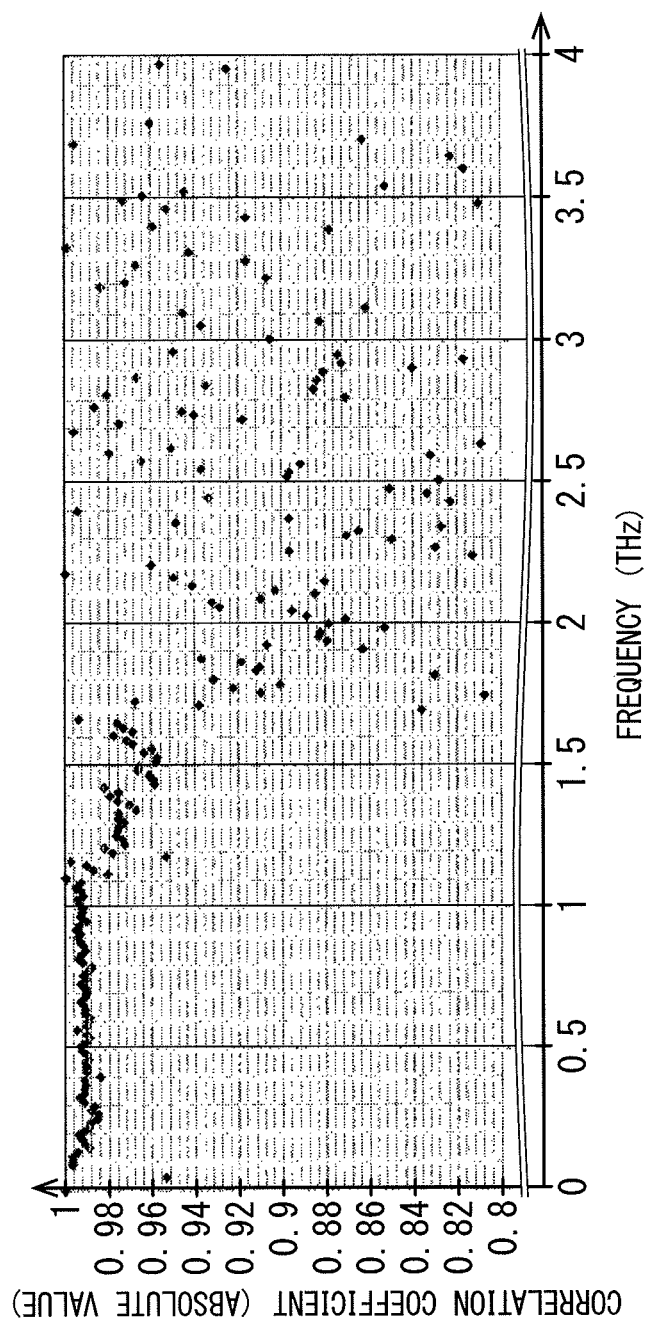
FIG. 9 illustrates correlation coefficients for each frequency, acquired on the basis of the time waveforms in FIG. 7.

FIG. 9 illustrates correlation coefficients for each frequency, acquired based on the time waveforms TW11 to TW14 illustrated in FIG. 7. Note that the correlation coefficients in FIG. 9 are converted into absolute values for illustration. The correlation coefficients illustrated in FIG. 9 are examples of measurement that is conducted using as a terahertz wave generator a dipole photoconductive switch 14 that generates the terahertz wave LT1 mainly in the range of 0.1 to 4 THz.

As illustrated in FIG. 9, it is clear that the correlation coefficients are high in the range of 0.1 to 1.6 THz. By using the terahertz wave LT1 in a frequency region with such high correlation coefficients, it is possible to acquire the accurate correlation information C1 and to accurately acquire the amount of a catalyst supported on the basis of the correlation information C1.

A configuration is also possible in which a band-pass filter is provided on the optical path of the transmitted terahertz wave LT2 to allow only part of the transmitted terahertz wave LT2 in the above frequency region with high correlation coefficients to be incident on the photoconductive switch 34. With this configuration, since the correlation information C1 is acquired on the basis of frequency components with high correlation coefficients, accuracy in the measurement of the amount of a catalyst supported can be improved. Such part of the transmitted terahertz wave in a frequency region with high correlation coefficients may be extracted through arithmetic processing, instead of using a band-pass filter. For example, a time waveform of the measured transmitted terahertz wave LT2 may be Fourier-transformed and developed in frequency regions, and only the above frequency region with high correlation coefficients may be inverse Fourier-transformed.

Amount-of-Catalyst-Supported Measuring Mode

Referring back to FIG. 6, the amount-of-catalyst-supported measuring mode will be described. In the following description, it is assumed that the sample 9 as an object to be measured is retained on the sample stage 20.

In the amount-of-catalyst-supported measuring mode for measuring the amount of a catalyst supported, processing for receiving designation of a point at which the amount of a catalyst supported is to be measured is first performed (step S13). As one example, in step S13, a measurement-point designation module, which is not shown, may display an input screen for designating a measurement point on the display part 61 to allow an operator to designate one or a plurality of points as measurement points. Such measurement points may be designated in units of regions. Or, measurement points may be fixed in advance. In this case, the processing in step S13 is omitted.

Next, the sample stage movement mechanism 24 moves the sample stage 20 so that the measurement point designated in step S13 is irradiated with the terahertz wave LT1 (step S14). Then, the sample 9 is irradiated with the terahertz wave LT1, and the transmitted-terahertz-wave detection part 30 detects the transmitted terahertz wave LT2 that have passed through the sample 9 (step S15; a terahertz-wave emitting step and a transmitted-terahertz-wave detection step). At this time, the delay part 40 is driven to acquire the electric field intensity of the transmitted terahertz wave LT2 for each different phase.

Then, the peak intensity identification module 507 identifies a peak intensity on the basis of the electric field intensities of the transmitted terahertz wave LT2 acquired in step S15 (step S16; a peak-intensity identification step). Then, the amount-of-catalyst-supported acquisition module 511 reads out the correlation information C1 acquired in step S12 from the storage unit 60 and receives data indicating the peak intensity acquired in step S16. The amount-of-catalyst-supported acquisition module 511 then acquires the amount of a catalyst supported on the metal catalyst layer formed on the sample 9 on the basis of these pieces of information (step S17; a readout step and an amount-of-catalyst-supported acquisition step).

Then, the controller 50 determines whether or not the measurement of the amount of a catalyst supported is completed for all points designated in step S13 (step S18). When the measurements for all designated points have not yet been completed (NO in step S18), the procedure returns to step S14 and the controller 50 causes the sample stage 20 to move in such a way that the remaining points that have not yet been measured are irradiated with the terahertz wave LT1.

For example, when part of or the entire region of the surface of the sample 9 is designated as a measurement point in step S13, the measuring apparatus 1 two-dimensionally scans the designated region with the terahertz wave LT1. Then, the amount of a catalyst supported is acquired on the basis of the peak intensity of the transmitted terahertz wave LT2 acquired for each measurement point. Through this processing, amount-of-catalyst-supported distribution data is acquired, which indicates the distribution of the amounts of a catalyst supported on the above designated region.

When the measurements for all of the designated points have been completed (YES in step S18), the procedure proceeds to step S19 and the controller 50 displays measured results on the display part 61 (step S19). For example, when one or a plurality of dispersed points are designated as measurement points in step S13, the amount of a catalyst supported on the one point or on each of the plurality of points is displayed as appropriate on the display part. When part of or the entire region of the surface of the sample 9 is designated as a measurement point, the image generation module 513 generates an amount-of-catalyst-supported distribution image that represents the distribution of the amounts of a catalyst supported. In the amount-of-catalyst-supported distribution image, the magnitudes of the amounts of a catalyst supported are visually expressed in, for example, different colors or patterns. The generated amount-of-catalyst-supported distribution image is displayed on the display part 61.

Figure 10:
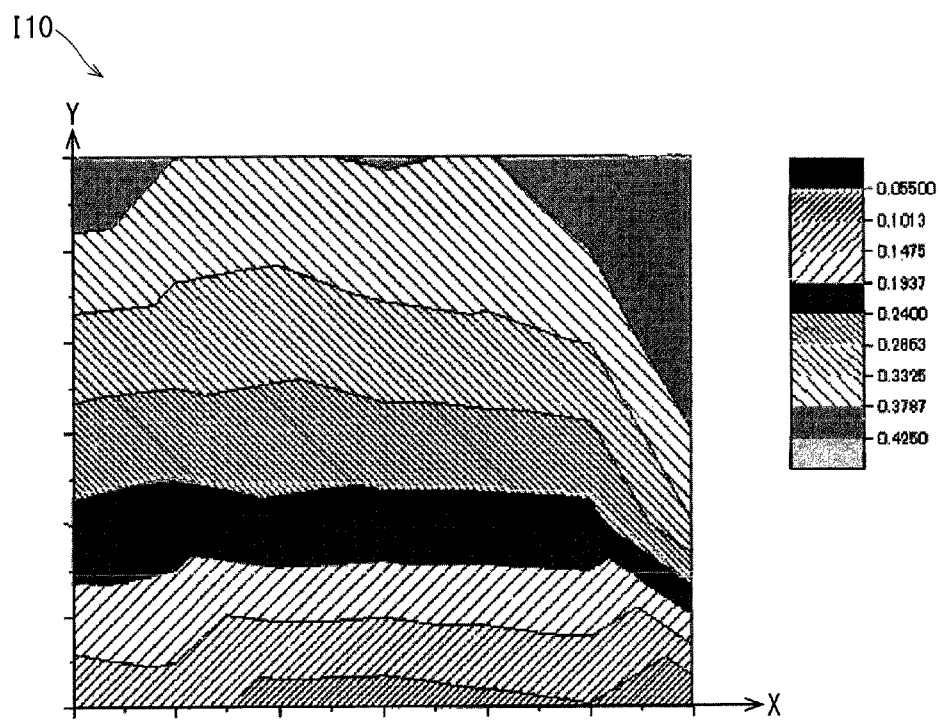
FIG. 10 illustrates an exemplary amount-of-catalyst-supported distribution image according to the first preferred embodiment.

FIG. 10 illustrates an exemplary amount-of-catalyst-supported distribution image 110 according to the first preferred embodiment. The amount-of-catalyst-supported distribution image 110 in FIG. 10 is an image that expresses the distribution of the amounts of a catalyst supported in two dimensions. The X and Y axes indicate two axial directions parallel to the surface of the sample 9. Each measurement point is colored or patterned depending on the magnitude of the amount of a catalyst supported. Such an amount-of-catalyst-supported distribution image 110 enables a user to easily visually recognize a change in the amount of a catalyst supported at each measurement point.

With the measuring apparatus 1 according to the present preferred embodiment, the amount of a catalyst supported can be monitored at the time when a membrane of a metal catalyst layer is formed on a base material. For example, the amount of a catalyst supported can be monitored at the time when an anode or cathode that includes a platinum catalyst is formed on an electrolyte membrane. It is thus possible to discover excess and deficiency of the amount of a catalyst supported, i.e., defective products, at an early stage and to reduce economic loss.

In the above description, the electric field intensity of the transmitted terahertz wave LT2 for each different phase is acquired at each measurement point in step S15 by moving the delay stage 43 of the delay part 40. Then, in step S16, the peak intensity is identified on the basis of the electric field intensity acquired for each phase. However, it is not always necessary to acquire the electric field intensity for each different phase at all measurement points. For example, the measurement of the transmitted terahertz wave LT2 may be conducted at a specific point on the sample 9 to identify a phase in which the transmitted terahertz wave LT2 has a peak intensity and to identify the position of the delay stage 43 that corresponds to the identified phase. Note that the position of the delay stage 43 may be identified by identifying a phase with the peak intensity at a plurality of points and averaging these phases. For the other measurement points, the position of the delay stage 43 is fixed at the above identified position to fix the timing of detection, and the electric field intensity of the transmitted terahertz wave LT2 is measured. The electric field intensity measured in this way may be used as the peak intensity of the transmitted terahertz wave LT1. By measuring the transmitted terahertz wave LT2 with the delay stage 43 fixed in this way, it is possible to shorten the time required to acquire the peak intensity of the transmitted terahertz wave LT2.

The delay stage 43 may also be fixed in step S11 when the transmitted terahertz wave LT2 is measured for each reference sample having a different amount of a catalyst supported in order to obtain the correlation information C1. A concrete example is such that a single (or a plurality of) reference sample is used to identify a phase in which the transmitted terahertz wave LT2 has a peak intensity and to identify the position of the delay stage 43 that corresponds to the identified phase. For the other reference samples, the transmitted terahertz wave LT2 may be measured with the delay stage 43 fixed at the previously identified position, and the measured value may be used as the peak intensity. With this configuration, it is possible to shorten the time required to measure the transmitted terahertz wave LT2 for each of the plurality of reference samples and to thereby increase the speed of acquiring the correlation information C1.

2. Second Preferred Embodiment

Next, a second preferred embodiment according to the present invention will be described. In the following description, components having the same functions as those described above are designated by the same reference numerals or characters or by the same reference numerals or characters with alphabetic characters appended thereto, and may not be described in detail.

Figure 11:
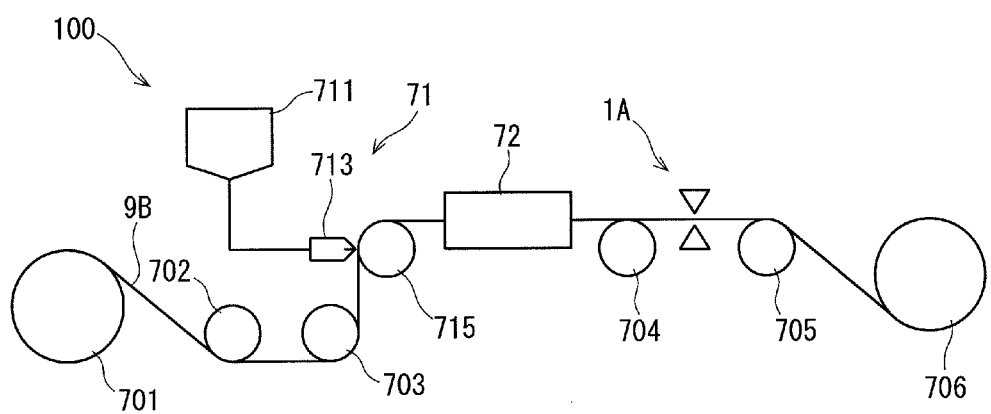
FIG. 11 is a schematic side view of a membrane forming system that incorporates a measuring apparatus according to a second preferred embodiment.

FIG. 11 is a schematic side view of a membrane forming system 100 that incorporates a measuring apparatus 1A according to a second preferred embodiment. The membrane forming system 100 is a system for forming a membrane of a metal catalyst layer on one side of a sheet-like base material 9B that is conveyed in a roll-to-roll process. The membrane forming system 100 includes the measuring apparatus 1A for measuring the amount of a catalyst supported, on a conveyance path of the base material 9B.

In the membrane forming system 100, the base material 9B unrolled from a feed roller 701 is conveyed through conveying rollers 702 and 703 to a coating part 71.

The coating part 71 includes a slit die coater 711, a coating-liquid supply part 713, and a support roller 715. The slit die coater 711 has a slit-like exhaust port that extends along the width of the base material 9B. The coating-liquid supply part 713 supplies a coating liquid that contains a metal catalyst to the slit die coater 711 through piping. The support roller 715 is located at a position facing the exhaust port of the slit die coater 711 and supports the rear surface of the base material 9B.

The base material 9B with the coating liquid applied by the coating part 71 is conveyed to a drying part 72. The drying part 72 is configured to perform dry processing for drying a coat of the coating liquid formed on one side of the base material 9B by the slit die coater 711 of the coating part 71. As one example, the drying part 72 may supply hot air to the base material 9B to heat the base material 9B and to evaporate moisture in the coating liquid or a solvent.

The base material 9B dried by the drying part 72 is conveyed through the conveying rollers 704 and 705 and rolled round a roll-up roller 706.

The measuring apparatus 1A is located at a position between the conveying rollers 704 and 705 and configured to measure the amount of a catalyst supported on the dried base material 9B (object to be measured). Note that the location of the measuring apparatus 1A is not limited to the above position. For example, the measuring apparatus 1A may be located at a position between the drying part 72 and the conveying roller 704 or at a position between the conveying roller 705 and the roll-up roller 706. The measuring apparatus 1A emits the terahertz wave LT1 to the base material 9B with a metal catalyst layer formed on one side after the dry processing, and detects the transmitted terahertz wave LT2 that is a transmitted terahertz wave. Note that the measuring apparatus 1A may be configured to emit the terahertz wave LT1 to the surface of the base material 9B on side where the membrane is formed, or may be configured to emit the terahertz wave LT1 to the opposite rear surface of the base material 9B.

The measuring apparatus 1A may be located at a position between the slit die coater 711 and the drying part 72 and configured to measure the transmitted terahertz wave LT2 that has passed through the metal catalyst layer before drying. When the metal catalyst layer contains a solvent (e.g., moisture) that absorbs the terahertz wave LT1, frequency components to be absorbed by the solvent may be excluded to identify the amount of a catalyst supported with high accuracy. Note that such specific frequency components may be excluded by using a predetermined band-pass filter provided on the optical path of the transmitted terahertz wave LT2 or may be excluded through computations. In the case of using computations, a time waveform of the transmitted terahertz wave LT2 may be Fourier-transformed and developed in frequency regions, and the frequency regions, excluding a specific frequency region, may be inverse Fourier-transformed.

The measuring apparatus 1A differs from the measuring apparatus 1 including the sample stage 20 in that the base material 9B as an object to be measured is a sheet-like material, and the base material 9B is supported by the conveying rollers 704 and 705. Although not shown, the other configuration of the measuring apparatus 1A is approximately similar to the configuration of the measuring apparatus 1 and includes the terahertz-wave emitting part 10, the transmitted-terahertz-wave detection part 30, the delay part 40, and the controller 50.

With the measuring apparatus 1A of the present preferred embodiment, it is also possible to identify the amount of a catalyst supported, on the basis of the peak intensity of the transmitted terahertz wave LT2 that has passed through the metal catalyst layer formed on the surface of the base material 9B and the correlation information acquired in advance. That is, the amount of a catalyst supported can be monitored at the time when an anode or cathode as a metal catalyst layer is formed on an electrolyte membrane. It is thus possible to discover excess and deficiency of the amount of a catalyst supported, i.e., defective products, at an early stage and to reduce economic loss.

In addition, non-contact/no-destructive inspection reduces waste due to sampling that occurs in conventional destructive inspection.

As described above, the transmitted terahertz wave LT2 may be measured with the delay stage 43 fixed at a position that is identified in advance and corresponds to a phase that takes the peak intensity. In this case, it is possible to acquire the peak intensity quickly and to acquire the amount of a catalyst supported in real time on the basis of the peak intensity and the correlation information C1.

Alternatively, the measuring apparatus 1A may be configured to be able to change a position to be irradiated with the terahertz wave LT1 by using, for example, the aforementioned galvanometer mirror.

The measuring apparatus 1A may also be configured to irradiate a plurality of points located at fixed intervals along the width of the base material 9B at the same time with the terahertz wave LT1 and to detect the transmitted terahertz wave LT2 at each point. For example, the terahertz wave LT1 emitted from the photoconductive switch 14 in FIG. 1 may be divided to irradiate a plurality of points along the width of the base material 9B. Alternatively, a plurality of photoconductive switches 14 may be prepared such that different positions are irradiated at the same time with the terahertz waves LT1 emitted from the respective photoconductive switches 14. With this configuration, it is possible to quickly detect the occurrence of, for example, uneven coating in a wide range.

3. Third Preferred Embodiment

FIG. 12 is a schematic configuration diagram of a measuring apparatus 1B according to a third preferred embodiment. The measuring apparatus 1B includes a reflected-terahertz-wave detection part 80 in addition to the configuration of the measuring apparatus 1 in FIG. 1. As will be described later, part of the terahertz wave LT1 is reflected by a metal catalyst contained in the metal catalyst layer formed on the sample 9, which is an object to be measured. The reflection position at which the terahertz wave LT1 is reflected at this time in the metal catalyst layer of the sample 9 depends on how the metal catalyst is distributed in the direction of membrane thickness of the metal catalyst layer. Thus, imbalances in the distribution of the metal catalyst in the direction of membrane thickness (i.e., the position of the center of gravity of the metal catalyst) can be measured by identifying the reflection position of the terahertz wave LT1 in the metal catalyst layer. Hereinafter, the configuration of the reflected-terahertz-wave detection part 80 will be described.

Reflected-Terahertz-Wave Detection Part

The reflected-terahertz-wave detection part 80 is configured to detect the electric field intensity of a reflected terahertz wave LT3 that is the terahertz wave LT1 reflected by the sample 9. To be more specific, wire grids 81 and 82 are provided on the optical path of the terahertz wave LT1 from the parabolic mirror 18 to the sample 9. The wire grids 81 and 82 are located to have different angles of polarization. As one example, the wire grid 81 may be located to form an angle of 90 degrees with respect to the angle of incidence of the terahertz wave LT1, and the wire grid 82 may be located to form an angle of 45 degrees with respect to the wire grid 81, as illustrated in FIG. 12. By setting the angles of polarization of the wire grids 81 and 82 to create an angle difference of 45 degrees therebetween, it is possible to minimize attenuation of the electric field intensity of the reflected terahertz wave LT3.

The terahertz wave LT1 that has passed through the wire grids 81 and 82 is incident on the sample stage 20, and part of the incident terahertz wave is reflected by the sample 9. The reflected terahertz wave LT3, which is the terahertz wave reflected, is reflected by the wire grid 82 and is incident on a parabolic mirror 83. The reflected terahertz wave LT3 reflected by the parabolic mirror 83 is caused to converge by the parabolic mirror 84 and is incident on a photoconductive switch 85.

When probe light LP3 that is incident through a delay part 40A is received, current that corresponds to the electric field intensity of the reflected terahertz wave LT3 incident on the photoconductive switch 85 flows through the photoconductive switch 85. The probe light LP3 is beam light produced by the beam splitter B2 dividing the probe light LP2. A change in voltage generated by the current flow through the photoconductive switch 85 is amplified by a lock-in amplifier 86 and incorporated in a controller 50A.

The delay part 40A includes plane mirrors 41A and 42A, a delay stage 43A, and a delay stage movement mechanism 44A and has an approximately similar configuration to the configuration of the delay part 40. The delay stage 43A is moved parallel to the direction of incidence of the probe light LP3 by the delay stage movement mechanism 44A. By linearly moving the delay stage 43A in parallel with the probe light LP3, the optical path length of the probe light LP3 from the femtosecond pulsed laser 11 to the photoconductive switch 85 can be changed. With this configuration, it is possible to change the timing of when the probe light LP3 is incident on the photoconductive switch 85. That is, it is possible to change the timing (phase) of when the photoconductive switch 85 detects the electric field intensity of the reflected terahertz wave LT3.

Figure 13:
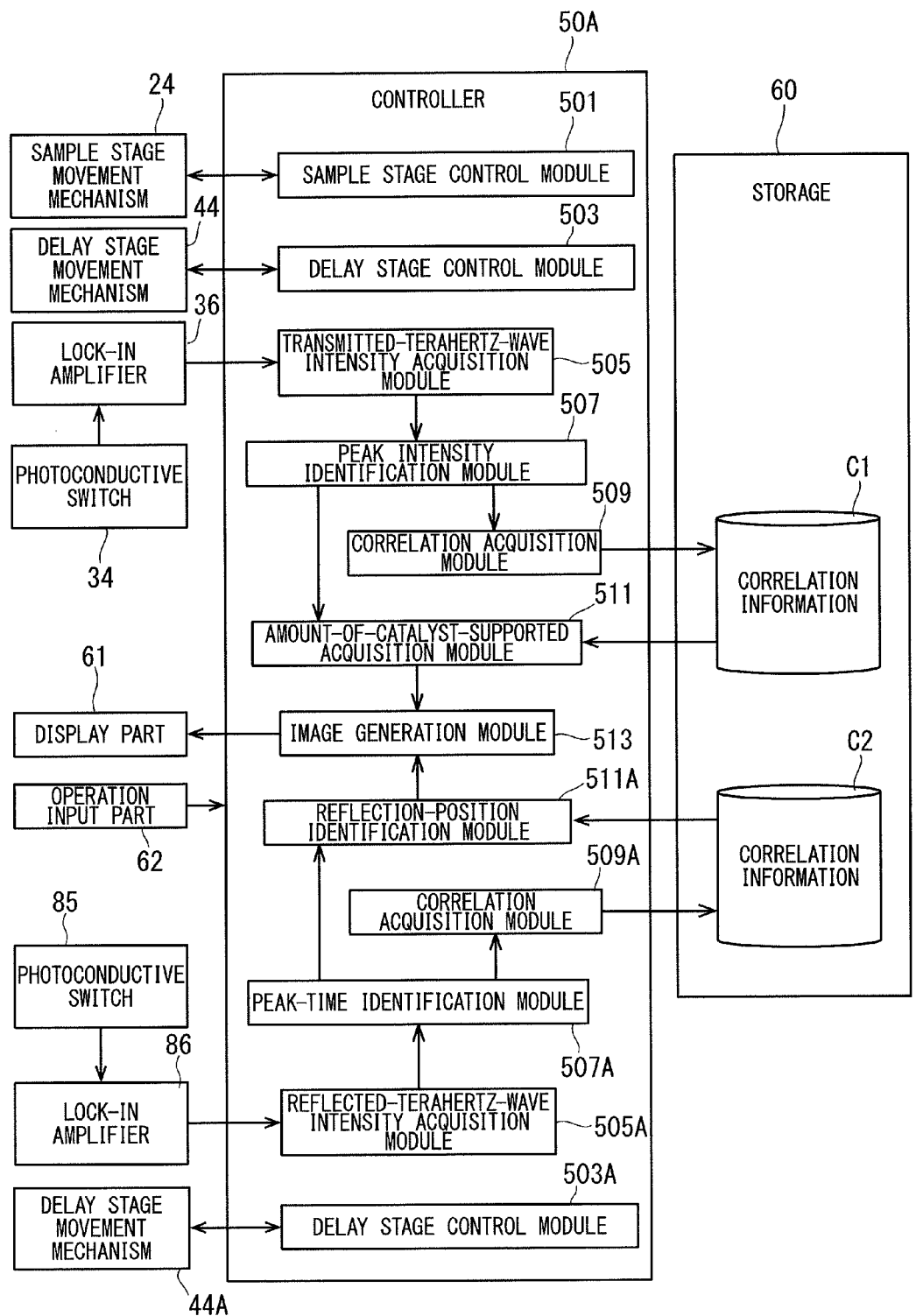
FIG. 13 is a block diagram illustrating a configuration of a controller according to the third preferred embodiment.

FIG. 13 is a block diagram illustrating a configuration of the controller 50A according to the third preferred embodiment. The controller 50A includes, in addition to the function modules of the controller 50, a delay stage control module 503A, a reflected-terahertz-wave intensity acquisition module 505A, a peak time identification module 507A, a correlation acquisition module 509A, and a reflection-position identification module 511A. These function modules are functions that are each implemented by the CPU operating in accordance with a program not shown. Note that some or all of these functions may be implemented by hardware such as dedicated circuits.

The delay stage control module 503A is configured to control the delay stage movement mechanism 44A.

The reflected-terahertz-wave intensity acquisition module 505A is configured to read the value of a voltage produced by the reflected terahertz wave LT3 detected by the photoconductive switch 85 via the lock-in amplifier 86. By reading the voltage value, the reflected-terahertz-wave intensity acquisition module 505A acquires the electric field intensity of the reflected terahertz wave LT3. As a result of the delay stage control module 503A moving the delay stage 43A of the delay part 40A, the reflected-terahertz-wave intensity acquisition module 505A acquires the electric field intensity of the reflected terahertz wave LT3 with different timings (phases).

The peak time identification module 507A is configured to identify the time (phase) at which the electric field intensity of the reflected terahertz wave becomes the peak intensity, on the basis of the electric field intensities acquired for different phases of the reflected terahertz wave LT3 by the reflected-terahertz-wave intensity acquisition module 505A. In the following description, the time with the peak intensity is referred to as a "peak time."

The correlation acquisition module 509A is configured to acquire correlation information C2 that indicates the correlation between the reflection position in the metal catalyst layer formed on the sample 9 and the peak time of the reflected terahertz wave LT3 reflected by the sample 9. The correlation information C2 is stored in the storage unit 60 and readable by the reflection-position identification module 511A.

As will be described, the measuring apparatus 1B prepares in advance samples (hereinafter, also referred to as "reference samples") that respectively include metal catalyst layers having different reflection positions of the reflected terahertz wave LT3. Then, the electric field intensity of the reflected terahertz wave LT3 is measured for each reference sample, and the peak time of the reflected terahertz wave LT3 that corresponds to each reflection position is identified by the peak time identification module 507A. The correlation acquisition module 509A acquires the correlation information C2 that identifies the correlation between the reflection position in each reference sample and the peak time acquired for the reference sample.

The correlation information C2 may be data in the form of a correspondence table in which the peak time of the reflected terahertz wave LT3 is recorded for each of several reflection positions, or may be data in the form of a relational expression between the reflection position and the peak time of the reflected terahertz wave LT3.

The reflection-position identification module 511A is configured to identify the reflection position of the terahertz wave LT1 in the sample 9 on the basis of the correlation information C2 stored in the storage unit 60 and the peak time of the reflected terahertz wave LT3 reflected by the sample 9.

The image generation module 513 is configured to display the measured result of the reflection position identified by the reflection-position identification module 511A on the display part 61. For example, the surface of the sample 9 is scanned with the terahertz wave LT1 to acquire the distribution of peak times of the terahertz wave LT1. On the basis of this distribution of peak times, the reflection-position identification module 511A acquires a two-dimensional distribution of reflection positions (depths). The image generation module 513 generates an image that expresses the two-dimensional distribution of the reflection positions in three dimensions.

Operations of Measuring Apparatus

Figure 14:
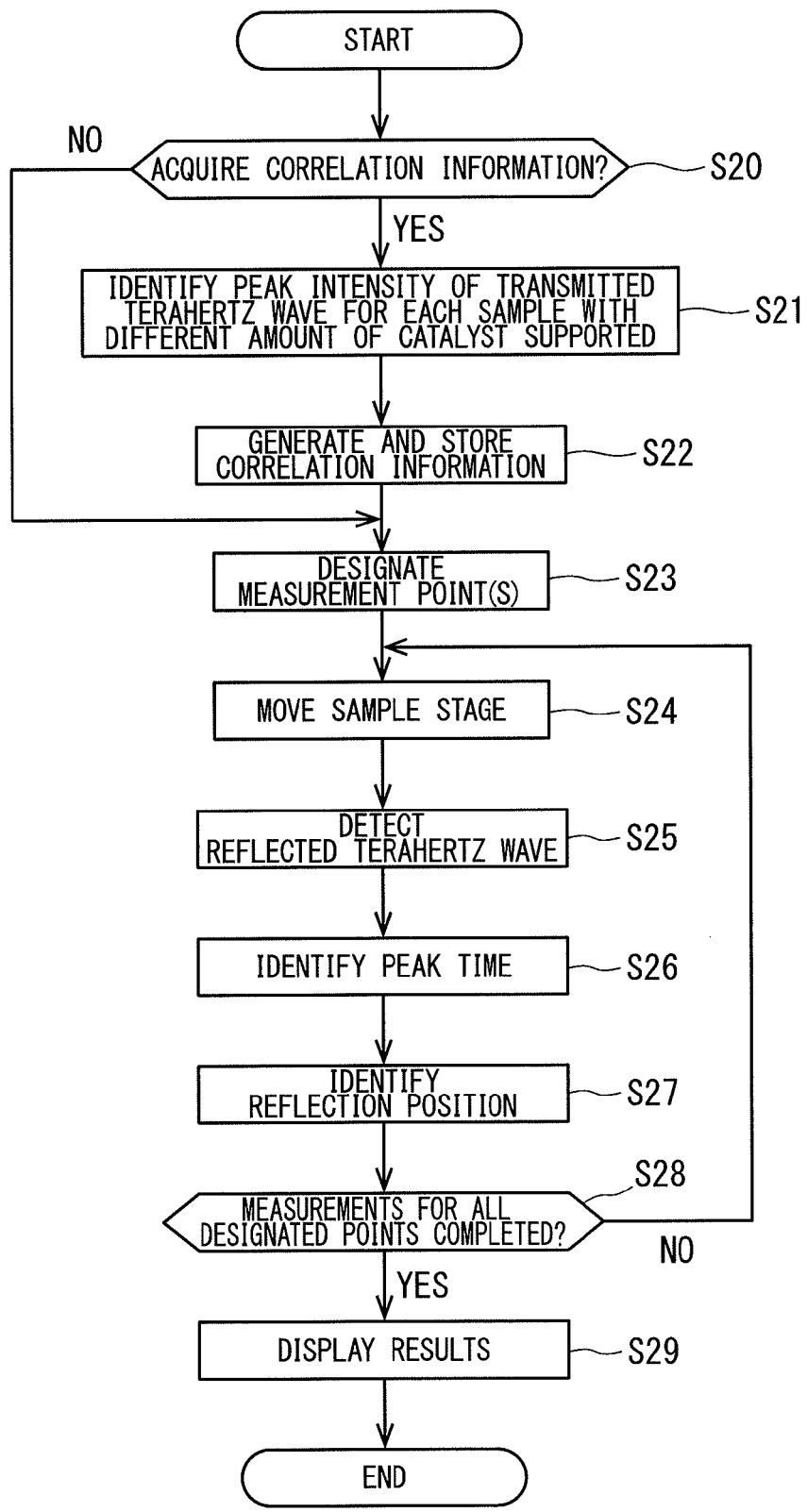
FIG. 14 is a flowchart illustrating a procedure of operations performed by the measuring apparatus according to the third preferred embodiment.

FIG. 14 is a flowchart illustrating a procedure of operations performed by the measuring apparatus 1B of the third preferred embodiment. It is assumed that the operations of the measuring apparatus 1B described below are performed under the control of the controller 50A in accordance with the procedure of operations, unless otherwise specified.

First, the controller 50A determines on the basis of an operator's instruction whether or not to acquire the correlation information C2 (step S20). If YES in step S20, the procedure proceeds to step S21 and the measuring apparatus 1B operates in a correlation-information acquisition mode for acquiring the correlation information C2. If NO in step S20, on the other hand, the procedure proceeds to step S23 and the measuring apparatus 1B operates in a reflection-position identification mode for identifying the reflection position.

Description of Principle of Change in Peak Time of Reflected Terahertz Wave

The principle of a change in the peak time of the reflected terahertz wave LT3 according to the distribution of the metal catalyst in the metal catalyst layer in the direction of membrane thickness will now be described.

In the Case of Uniform Distribution of Metal Catalyst

Figure 15:
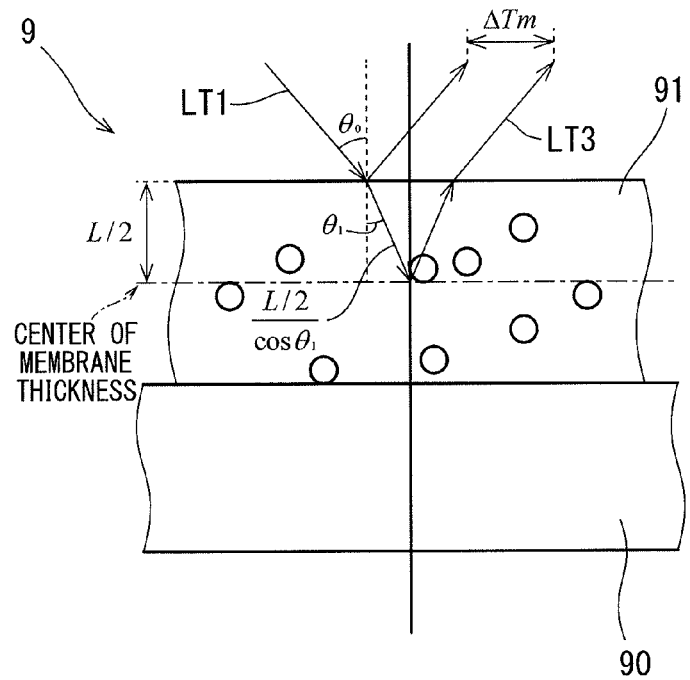
FIG. 15 is a schematic cross-sectional view of a sample in which a metal catalyst is uniformly distributed in the direction of membrane thickness.

FIG. 15 is a schematic cross-sectional view of the sample 9 in which the metal catalyst is uniformly distributed in the direction of membrane thickness. The sample 9 has a configuration in which a metal catalyst layer 91 is layered on the upper surface of a base material 90.

In the following description, the absolute refractive index in the air is given as "1", the light velocity in the air is given as "c", the absolute refractive index in the metal catalyst layer 91 is given as "n", the light velocity in the metal catalyst layer 91 is given as "v", the membrane thickness of the metal catalyst layer 91 is given as "L", the angle of incidence is given as "$\theta_0$", and the angle of refraction is given as "$\theta_1$".

Equation 1 holds true according to the Snell's law.

$$\frac{\sin\theta_0}{\sin\theta_1} = \frac{c}{v} = n \quad \text{[Equation 1]}$$

When the metal catalyst is uniformly distributed in the metal catalyst layer 91 as illustrated in FIG. 15, the position of the center of gravity of the amount of a catalyst supported is in the center of membrane thickness, i.e., at a position that is L/2 away from the surface of the membrane. Thus, a distance L' of travel of the terahertz wave LT1 in the metal catalyst layer 91 is expressed by Equation (2).

$$L' = \frac{2 \cdot L/2}{\cos\theta_1} = \frac{L}{\cos\theta_1} \quad \text{[Equation 2]}$$

Accordingly, a delay time ΔTm by which the reflected terahertz wave LT3 reflected at the position of the center of gravity of the metal catalyst layer 91 is delayed with respect to the terahertz wave LT1 travelling in the air is expressed by Equation (3).

$$\Delta Tm = \frac{L/\cos\theta_1}{v} \quad \text{[Equation 3]}$$

Equation (4) is obtained from Equation (1) (Snell's Equation).

$$\cos\theta_1 = \sqrt{1 - \left(\frac{\sin\theta_0}{n}\right)^2} \quad \text{[Equation 4]}$$

When Equation (4) is applied to Equation (3), $\Delta Tm$ is expressed by Equation (5).

$$\Delta Tm = \frac{L}{\frac{c}{n} \cdot \frac{\sqrt{n^2 - \sin^2\theta_0}}{n}} = \frac{n^2 L}{c\sqrt{n^2 - \sin^2\theta_0}} \quad \text{[Equation 5]}$$

In the Case of Uneven Distribution of Metal Catalyst on Surface Side

Figure 16:
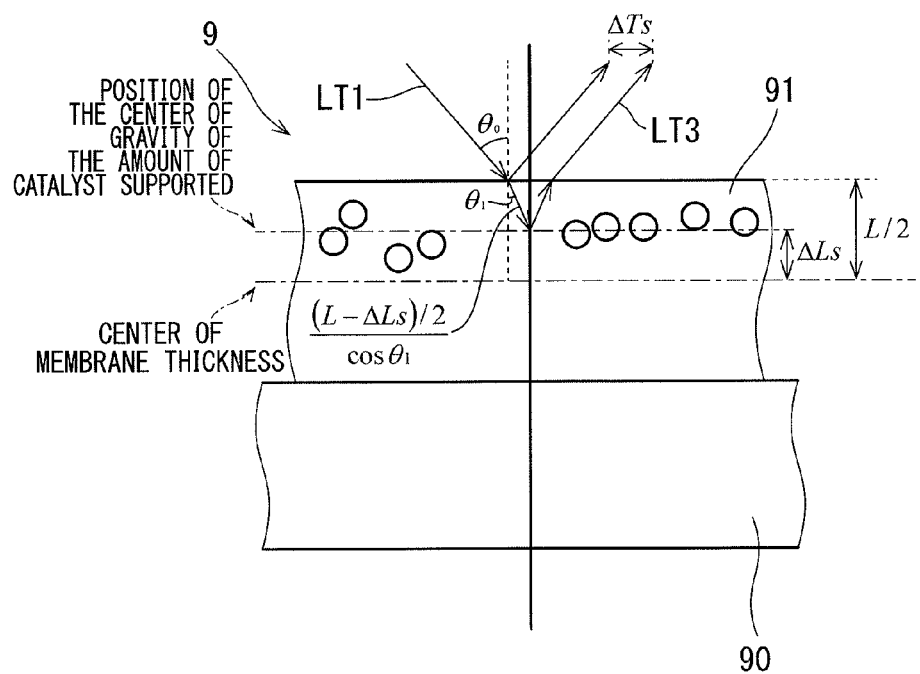
FIG. 16 is a schematic cross-sectional view of a sample in which a metal catalyst is unevenly distributed toward the surface in the direction of membrane thickness.

FIG. 16 is a schematic cross-sectional view of the sample 9 in which the metal catalyst is unevenly distributed on the surface side in the direction of membrane thickness. In the present example, it is assumed that the position of the center of gravity of the amount of a catalyst supported on the metal catalyst layer 91 in the direction of membrane thickness tilts by $\Delta Ls$ toward the surface from the center of the membrane thickness. A distance Ls of travel of the terahertz wave LT1 in the metal catalyst layer 91 is expressed by Equation (6).

$$Ls = \frac{2(L/2 - \Delta Ls)}{\cos\theta_1} = \frac{L - 2\Delta Ls}{\cos\theta_1} \quad \text{[Equation 6]}$$

A delay time $\Delta Ts$ by which the reflected terahertz wave LT3 reflected at the position of the center of gravity of the metal catalyst layer 91 is delayed with respect to the terahertz wave LT1 travelling in the air is expressed by Equation (7).

$$\Delta Ts = \frac{L - 2\Delta Ls}{\frac{c}{n} \cdot \frac{\sqrt{n^2 - \sin^2\theta_0}}{n}} = \frac{n^2(L - 2\Delta Ls)}{c\sqrt{n^2 - \sin^2\theta_0}} \quad \text{[Equation 7]}$$

As is clear from the comparison between $\Delta Tm$ expressed by Equation (5) and $\Delta Ts$ expressed by Equation (7), the delay time decreases as the position of the center of gravity of the amount of a catalyst supported on the metal catalyst layer 91 gets closer to the surface.

In the Case of Uneven Distribution of Metal Catalyst on Interface Side

Figure 17:
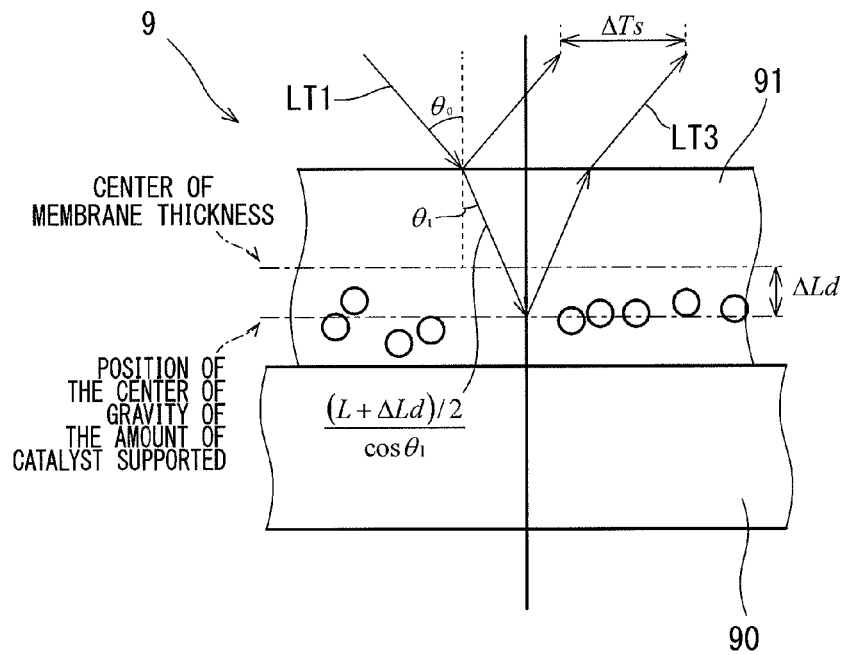
FIG. 17 illustrates a sample in which a metal catalyst is unevenly distributed toward the interface in the direction of membrane thickness.

FIG. 17 illustrates the sample 9 in which the metal catalyst is unevenly distributed on the interface side in the direction of membrane thickness. In the present example, it is assumed that the position of the center of gravity of the amount of a catalyst supported on the metal catalyst layer 91 tilts by $\Delta Ld$ toward the interface (i.e., a boundary plane between the base material 90 and the metal catalyst layer 91) from the center of the membrane thickness. A distance Ld of travel of the terahertz wave LT1 in the metal catalyst layer 91 is expressed by Equation (8).

$$Ld = \frac{2(L/2 + \Delta Ld)}{\cos\theta_1} = \frac{L + 2\Delta Ld}{\cos\theta_1} \quad \text{[Equation 8]}$$

A delay time $\Delta Td$ by which the reflected terahertz wave LT3 reflected at the position of the center of gravity of the metal catalyst layer 91A is delayed with respect to the terahertz wave LT1 travelling in the air is expressed by Equation (9).

$$\Delta Td = \frac{L + 2\Delta Ld}{\frac{c}{n} \cdot \frac{\sqrt{n^2 - \sin^2\theta_0}}{n}} = \frac{n^2(L + 2\Delta Ld)}{c\sqrt{n^2 - \sin^2\theta_0}} \quad \text{[Equation 9]}$$

As is clear from the comparison between $\Delta Tm$ expressed by Equation (5) and $\Delta Td$ expressed by Equation (9), the delay time increases as the position of the center of gravity of the amount of a catalyst supported on the metal catalyst layer 91 gets closer to the interface.

Figure 18:
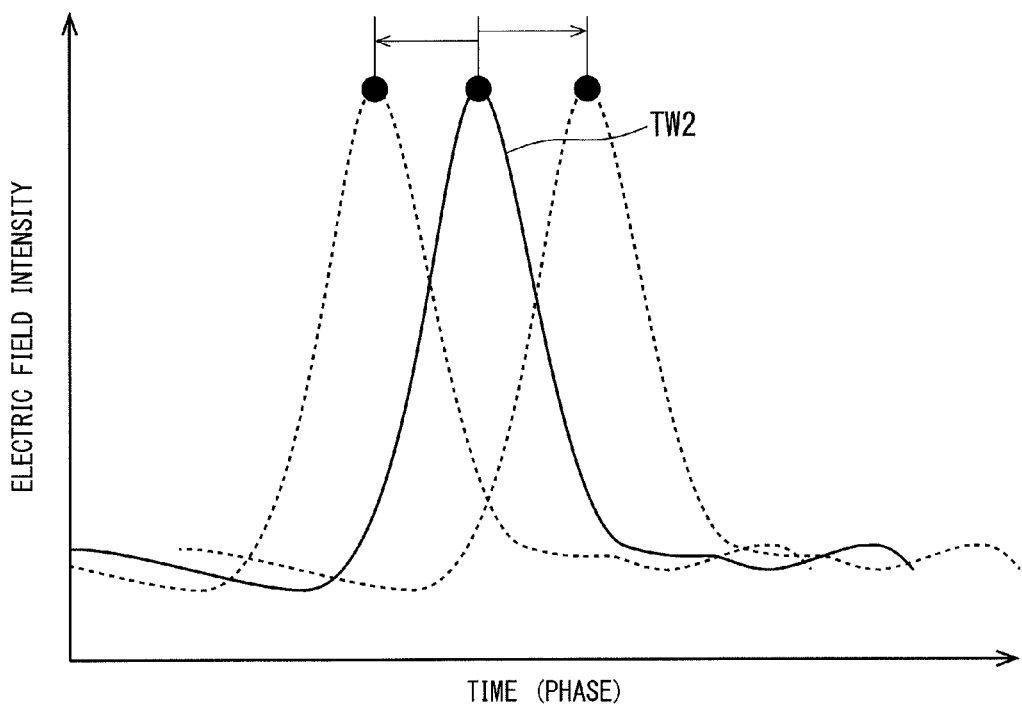
FIG. 18 illustrates time waveforms for reflected terahertz waves that are measured by the measuring apparatus according to the third preferred embodiment.

FIG. 18 illustrates the time waveform TW2 of the reflected terahertz wave LT3 measured by the measuring apparatus 1B of the third preferred embodiment. The reflection position of the terahertz wave LT1 in the metal catalyst layer changes with a change in the position of the center of gravity of the amount of a catalyst supported. As the reflection position gets closer to the surface, the reflected terahertz wave LT3 arrives earlier at the photoconductive switch 85. Consequently, the time waveform TW2 of the reflected terahertz wave LT3 is shifted to the left as illustrated in FIG. 18. On the other hand, as the reflection position gets closer to the interface, the reflected terahertz wave LT3 arrives later at the photoconductive switch 85, and the time waveform TW2 is shifted to the right. Accordingly, a change in the reflection position of the terahertz wave LT1, i.e., the position of the center of gravity of the amount of a catalyst supported, can be measured quantitatively by measuring the early or late arrival time of the time waveform TW2.

Note that the early or late arrival time of the time waveform TW2 may preferably be measured by detecting a change in the time (peak time) when the reflected terahertz wave LT3 has a peak intensity as illustrated in FIG. 18. It is, of course, possible to identify the early or late arrival time by identifying the time when the reflected terahertz wave LT3 has an intensity other than the peak intensity.

Base on the principle described above, in step S21 in FIG. 14, the peak time of the reflected terahertz wave LT3 is identified for each reference sample with a different reflection position of the terahertz wave LT1 (i.e., the position of the center of gravity of the amount of a catalyst supported). Then, the correlation information C2 indicating the correlation between the reflection position of the terahertz wave LT1 and the peak time is acquired in step S22.

Note that such reference samples having different positions of the center of gravity of the amount of a catalyst supported may be obtained, for example, in such a manner that coating liquids that contain metal catalysts with different densities are applied in layers at the time of forming metal catalyst layers. For example, a reference sample in which the position of the center of gravity of the amount of a catalyst supported tilts toward the surface may be obtained by first forming a low-density metal catalyst layer and then forming a high-density metal catalyst layer on the low-density metal catalyst layer. Also, a reference sample in which the position of the center of gravity of the amount of a catalyst supported tilts toward the interface may be obtained by first forming a high-density metal catalyst layer and then forming a low-density metal catalyst layer on the high-density metal catalyst layer.

Reflection-Position Identification Mode

Next, the reflection-position identification mode will be described. In the following description, it is assumed that the sample 9, as an object for which the reflection position of the terahertz wave LT1 (i.e., the position of the center of gravity of the amount of a catalyst supported) is to be identified, is retained on the sample stage 20.

In the reflection-position identification mode, processing for receiving designation of a measurement point at which a reflection position is to be identified is first performed (step S23). This step S23 is approximately similar processing to step S13 described with reference to FIG. 6.

Next, the sample stage movement mechanism 24 moves the sample stage 20 in such a manner that the measurement point designated in step S23 is irradiated with the terahertz wave LT1 (step S24). Then, the sample 9 is irradiated with the terahertz wave LT1, and the reflected-terahertz-wave detection part 80 detects the reflected terahertz wave LT3 reflected from the sample 9 (step S25). At this time, the delay part 40A is driven to acquire the electric field intensity of the reflected terahertz wave LT3 for each different phase.

Then, the peak time identification module 507A identifies a peak time on the basis of the electric field intensities of the reflected terahertz wave LT3 acquired in step S25 (step S26). Then, the reflection-position identification module 511A reads out the correlation information C2 acquired in step S22 from the storage unit 60 and receives data that indicates the peak time acquired in step S26. On the basis of these pieces of information, the reflection-position identification module 511A identifies the reflection position of the terahertz wave LT1 on the sample 9 (step S27).

Then, the controller 50A determines whether or not the measurement of the amount of a catalyst supported has been completed for all points designated in step S23 (step S28).

When the measurements for all designated points have not yet been completed (NO in step S28), the procedure returns to step S24 and the controller 50A causes the sample stage 20 to be moved in such a manner that each remaining point that has not yet been measured is irradiated with the terahertz wave LT1.

For example, when part of or the entire region of the surface of the sample 9 is designated as a measurement point in step S23, the measuring apparatus 1B two-dimensionally scans the designated region with the terahertz wave LT1. Then, the reflection position is identified on the basis of the peak time of the reflected terahertz wave LT3 identified for each measurement point. Through this processing, reflection-position distribution data that indicates the distribution of reflection positions in the above designated region is acquired.

When the measurements for all of the designated points have been completed (YES in step S28), the procedure proceeds to step S29 and the controller 50A displays measured results on the display part 61 (step S29). For example, when one or a plurality of dispersed points are designated as measurement points in step S23, the reflection position at the one point or at each of the plurality of points is displayed as appropriate on the display part. When part of or the entire region of the surface of the sample 9 is designated as a measurement point, the image generation module 513 generates a reflection-position distribution image that represents the distribution of the reflection positions. The reflection-position distribution image is then displayed on the display part 61. The image generation module 513 is one example of a reflection-position distribution image generation part.

FIG. 19 illustrates an exemplary reflection-position distribution image 120 according to the third preferred embodiment. The reflection-position distribution image 120 illustrated in FIG. 19 is an image that expresses the distribution of reflection positions on a three-dimensional graph. The X and Y axes indicate two axial directions parallel to the surface of the sample 9, and the Z axis indicates the direction of membrane thickness of the sample 9. To be more specific, reflection positions at every measurement point are plotted on three-dimensional coordinates, and plotted points that are adjacent to one another in the X and Y axial directions are connected by straight lines. In this way, the reflection-position distribution image 120 enables a user to easily visually recognize a change in the reflection position at each measurement point.

In the measuring apparatus 1B, part of the terahertz wave LT1 emitted from the terahertz-wave emitting part 10 toward the sample 9 makes the transmitted terahertz wave LT2 that have passed through the sample 9, and the other part makes the reflected terahertz wave LT3. Accordingly, the reflected-terahertz-wave detection part 80 is able to detect the reflected terahertz wave LT3 at the same time as the transmitted-terahertz-wave detection part 30 detects the transmitted terahertz wave LT2. Accordingly, the measuring apparatus 1B enables simultaneous measurement of the amount of a catalyst supported on the metal catalyst layer in the sample 9 and the position of the center of gravity of the amount of a catalyst supported.

Note that the reflected-terahertz-wave detection part 80 according to the third preferred embodiment is also applicable to the measuring apparatus 1A of the second preferred embodiment illustrated in FIG. 11. In this case, the reflection position of the terahertz wave LT1 in the metal catalyst layer formed on one side of the base material 9B that is being conveyed in a roll-to-roll process can be identified by detecting the peak time of the reflected terahertz wave LT3. It is thus possible to identify the position of the center of gravity of the metal catalyst in the metal catalyst layer of an intermediate product during manufacture.

4. Variations

While the above has been a description of embodiments, the present invention is not limited to the embodiments described above, and may be modified in various ways.

For example, in the measuring apparatus 1 of the first preferred embodiment, the peak intensity (maximum intensity) of the transmitted terahertz wave LT2 is used to generate the correlation information C1 and identify the amount of a catalyst supported on the sample 9. However, the identification of the amount of a catalyst supported does not necessarily have to be based on the peak intensity. For example, correlation information may be generated by identifying a minimum value for the electric field intensity of the transmitted terahertz wave LT2 for each reference sample. In this case, the amount of a catalyst supported is identified on the basis of that correlation information and the minimum value of the transmitted terahertz wave LT2 measured for the sample 9. Alternatively, correlation information that indicates the correlation between the value of time quadrature and the amount of a catalyst supported may be acquired by integrating the electric field intensity with respect to time to acquire the value of time quadrature for each of the time waveforms TW11 to TW14 of the transmitted terahertz wave LT2 illustrated in FIG. 7. In this case, the amount of a catalyst supported is identified on the basis of that correlation information and the value of time quadrature of the transmitted terahertz wave LT2 measured for the sample 9.

In the measuring apparatus 1B of the third preferred embodiment, the peak time of the reflected terahertz wave LT3 (i.e., the time at which the reflected terahertz wave LT3 has the peak intensity) is used to generate the correlation information C2 and identify the reflection position of the terahertz wave LT1 on the sample 9. Alternatively, a configuration is also possible in which correlation information is generated by identifying a time at which the electric field intensity becomes a minimum for each reference sample, and the reflection position is identified on the basis of the correlation information and the time at which the electric field intensity becomes a minimum for the sample 9.

While the invention has been shown and described in detail, the foregoing description is in all aspects illustrative and not restrictive. It is therefore understood that numerous modifications and variations can be devised without departing from the scope of the invention. The configurations of the above-described embodiments and variations may be appropriately combined or omitted as long as there are no mutual inconsistencies.

What is claimed is:

1. A measuring apparatus for measuring an amount of a metal catalyst supported on an object to be measured, the object having a membrane of a metal catalyst layer containing said metal catalyst, comprising:
    a terahertz-wave emitting part that emits a terahertz wave in a range of 0.01 to 10 THz to an object to be measured;
    a transmitted-terahertz-wave detection part that detects an electric field intensity of a transmitted terahertz wave that is said terahertz wave that has passed through said object to be measured;
    a storage that stores first correlation information that is acquired in advance and indicates a correlation between the amount of said metal catalyst supported on said object to be measured and the electric field intensity of said transmitted terahertz wave;
    an amount-of-catalyst-supported acquisition part that acquires the amount of said metal catalyst supported on said object to be measured, on the basis of said first correlation information and the electric field intensity of said transmitted terahertz wave detected by said-transmitted-terahertz-wave detection part;
    a reflected-terahertz-wave detection part that detects an electric field intensity of a reflected terahertz wave that is said terahertz wave that is reflected from said object to be measured;
    wherein said storage stores second correlation information that is acquired in advance from reference samples with different positions of a center of gravity of the amount of said metal catalyst supported, and indicates a correlation between a reflection position in a direction of membrane thickness of the object to be measured from which the terahertz wave is reflected and a peak time when said reflected terahertz wave detected by said terahertz wave has a peak intensity, and
    said measuring apparatus further comprising:
    a reflection-position information acquisition part that acquires information regarding a reflection position in a direction of membrane thickness of said object to be measured, from which said terahertz wave is reflected and acquires a position of a center of gravity of the amount of said metal catalyst supported on said object to be measured from which said terahertz wave is reflected, on the basis of said second correlation information, the electric field intensity of said reflected terahertz wave detected by said reflected-terahertz-wave detection part, and the peak time when said reflected terahertz wave has the peak intensity.

2. The measuring apparatus according to claim 1, further comprising:
    a femtosecond pulsed laser, wherein
    said terahertz-wave emitting part includes a terahertz wave generator that generates said terahertz wave in a pulsed form upon receipt of first pulsed light emitted from said femtosecond pulsed laser, and
    said transmitted-terahertz-wave detection part includes a transmitted terahertz wave detector that detects the electric field intensity of said transmitted terahertz wave upon receipt of second pulsed light emitted from said femtosecond pulsed laser, and
    said measuring apparatus further comprising:
    a delay part that delays a time when said second pulsed light is incident on said transmitted terahertz wave detector with respect to a time when said first pulsed light is incident on said terahertz wave generator.

3. The measuring apparatus according to claim 2, further comprising:
    a peak-intensity identification part that identifies a peak intensity of the electric field intensity of said transmitted terahertz wave on the basis of electric field intensities of said transmitted terahertz wave that are acquired for different phases by controlling said delay part,
    wherein said amount-of-catalyst-supported acquisition part acquires the amount of said metal catalysts supported on said object to be measured, on the basis of said peak intensity and said first correlation information.

4. The measuring apparatus according to claim 1, further comprising:
    an amount-of-catalyst-supported distribution image generation part that generates an image of a distribution of said amount of said metal catalyst supported acquired by said amount-of-catalyst-supported acquisition part, on the basis of the electric field intensity of said transmitted terahertz wave that is acquired by scanning a surface of said object to be measured with said terahertz wave.

5. The measuring apparatus according to claim 1, further comprising:
    a reflection-position distribution image generation part that generates an image of a distribution of said reflection position acquired by said reflection-position information acquisition part, on the basis of said reflected terahertz wave detected by scanning a surface of said object to be measured with said terahertz wave.

6. A measuring method of measuring an amount of a metal catalyst supported on an object to be measured, the object having a metal catalyst layer containing said metal catalyst, the measuring methods comprising:
    a terahertz-wave emitting step (a) of emitting a terahertz wave in a range of 0.01 to 10 THz to an object to be measured;
    a transmitted-terahertz-wave detection step (b) of detecting an electric field intensity of a transmitted terahertz wave that is said terahertz wave that has passed through said object to be measured;
    a readout step (c) of reading out correlation information that is stored in advance in a storage and indicates a first correlation between the amount of said metal catalyst supported on said object to be measured and the electric field intensity of said transmitted terahertz wave;

an amount-of-catalyst-supported acquisition step (d) of acquiring the amount of said metal catalyst supported on said object to be measured, on the basis of said first correlation information and the electric field intensity of said transmitted terahertz wave acquired in said transmitted-terahertz-wave detection step, a reflected-terahertz-wave detection step (e) of detecting an electric field intensity of a reflected terahertz wave that is said terahertz wave that is reflected from said object to be measured;

storing second correlation information that is acquired in advance from reference samples with different positions of a center of gravity of the amount of said metal catalyst supported, and indicates a correlation between a reflection position in a direction of membrane thickness of the object to be measured from which the terahertz wave is reflected and a peak time when said reflected terahertz wave detected by said terahertz wave has a peak intensity, and a reflection-position information acquisition step (f) of acquiring information regarding a reflection position in a direction of membrane thickness of said object to be measured from which said terahertz wave is reflected and acquiring a position of a center of gravity of the amount of said metal catalyst supported on said object to be measured from which said terahertz wave is reflected, on the basis of said second correlation information, the electric field intensity of said reflected terahertz wave detected by said reflected-terahertz-wave detection part and the time when said reflected terahertz wave has the peak intensity.

* * * * *